US007018340B2

(12) United States Patent
Jaffe et al.

(10) Patent No.: US 7,018,340 B2
(45) Date of Patent: *Mar. 28, 2006

(54) APPARATUS AND METHOD FOR NON-INVASIVELY MEASURING CARDIAC OUTPUT

(75) Inventors: Michael B. Jaffe, Cheshire, CT (US); Joseph A. Orr, Salt Lake City, UT (US); Scott A. Kofoed, Salt Lake City, UT (US); Dwayne Westenskow, Salt Lake City, UT (US)

(73) Assignee: NTC Technology Inc., Wilmington, DE (US)

( * ) Notice: Subject to any disclaimer, the term of this patent is extended or adjusted under 35 U.S.C. 154(b) by 40 days.

This patent is subject to a terminal disclaimer.

(21) Appl. No.: 10/657,577

(22) Filed: Sep. 8, 2003

(65) Prior Publication Data

US 2004/0059239 A1 Mar. 25, 2004

Related U.S. Application Data

(60) Division of application No. 09/777,629, filed on Feb. 6, 2001, now Pat. No. 6,648,832, which is a continuation of application No. 09/262,510, filed on Mar. 2, 1999, now Pat. No. 6,227,196, which is a continuation-in-part of application No. 08/770,138, filed on Dec. 19, 1996, now Pat. No. 6,306,098.

(51) Int. Cl.
*A61B 5/00* (2006.01)

(52) U.S. Cl. .............................. 600/532; 73/23.3; 42/84
(58) Field of Classification Search ................ 600/532; 73/23.3; 422/84
See application file for complete search history.

(56) References Cited

U.S. PATENT DOCUMENTS 3,910,261 A 10/1975 Ragsdale et al.
4,192,301 A 3/1980 Hardwick
4,239,038 A 12/1980 Holmes (Continued)

FOREIGN PATENT DOCUMENTS

WO       WO 98/12963       4/1998

OTHER PUBLICATIONS

Winkler, Tito, et al., *Pulmonary Capillary Blood Flow by Partial $CO_2$ Rebreathing: A Simulation Study Using a Bicompartmental Model of Gas Exchange*, 1 page.

de Abreu, M. Gama, et al., *Reliability of the Partial $CO_2$ Rebreathing Technique for Measurement of Cardiac Output*, Proceedings RC IEEE–EMBS & 14th BMESI—1995 (3 pages).

(Continued)

*Primary Examiner*—Robert L. Nasser
(74) *Attorney, Agent, or Firm*—TraskBritt, PC

(57) ABSTRACT

Apparatus and methods for non-invasively determining the cardiac output or pulmonary capillary blood flow of a patient using partial re-breathing techniques. The apparatus includes a substantially instantaneously adjustable deadspace volume for accommodating differences in sizes or breathing capacities of various patients. The apparatus may be constructed of inexpensive elements, including one or more two-way valves, which render the apparatus very simple to use and inexpensive so that the unit may be employed as a disposable product. The method of the invention includes estimating the cardiac output or pulmonary capillary blood flow of a patient based on partial pressure of alveolar $CO_2$, rather than on the partial pressure of end tidal $CO_2$, as previously practiced. A computer program for calculating the cardiac output or pulmonary capillary blood flow of a patient is also disclosed.

17 Claims, 12 Drawing Sheets

U.S. PATENT DOCUMENTS

| | | | |
|---|---|---|---|
| 4,265,235 | A | 5/1981 | Fukunaga et al. |
| 4,941,476 | A | 7/1990 | Fisher |
| 4,947,860 | A | 8/1990 | Fisher |
| 4,949,724 | A | 8/1990 | Mahutte et al. |
| 5,299,579 | A | 4/1994 | Gedeon et al. |
| 5,642,726 | A | 7/1997 | Owens et al. |
| 5,752,509 | A | 5/1998 | Lachmann et al. |
| 5,782,774 | A | 7/1998 | Shmulewitz |
| 5,836,300 | A | 11/1998 | Mault |
| 5,971,934 | A | 10/1999 | Scherer et al. |
| 6,003,511 | A | 12/1999 | Fukunaga et al. |
| 6,251,082 | B1 * | 6/2001 | Rayburn .................. 600/532 |
| 6,648,831 | B1 * | 11/2003 | Orr et al. ................ 600/526 |

OTHER PUBLICATIONS de Abreu, Marcel Gama, et al., *Partial carbon dioxide breathing: A reliable technique for noninvasive measurement of nonshunted pulmonary capillary blood flow*, Crit Care med 1997, vol. 25, 4, p. 675–683.

Osterlund, B., et al., *A new method of using gas exchange measurements for the noninvasive determination of cardiac output: clinical experiences in adults following cardiac surgery*, Acta Anaesthesiologica Scandinavica 39 (1995), pp. 727–732.

Gedeon, A., et al., *Noninvasive Cardiac Output Determined with a New Method Based on Gas Exchange Measurements and Carbon Dioxide Rebreathing: A Study in Animals/Pigs,*, Journal of Clinical Monitoring, vol. 8, No. 4, Oct. 1992, pp. 267–278.

Gedeon, A., et al., *A new method for noninvasive bedside determination of pulmonary blood flow*Medical & Biological Engineering & Computing, Jul. 1980, pp. 411–418.

de Abreu, Marcelo Gama, et al., *Measurement of Pulmonary Capillary Blood Flow for Trending Mixed Venous Blood Oxygen Saturation and Oxygen Delivery*, 1 page.

Article entitled "Noninvasive Measurement of Cardiac Output Using Partial $CO_2$ Rebreathing" by John M. Capek and Rob J. Roy (pp. 653–661)– Printed in IEEE Transactions On Biomedical Engineering, vol. 35, No. 9—Sep. 1988.

Article entitled "Noninvasive Measurement of Cardiac Output Using Partial Carbon–Dioxide Rebreathing" by John Michael Capek (title, introductory pages and pp. 127–132)—Printed by UMI Dissertation Services—Dec. 1988.

Article entitled "Noninvasive Pulmonary Blood Flow for Optimal Peep" by A. Gedeon, ICOR AB, Ulvsundavägen 178 B, S–161 30 Bromma, Sweden (pp. 49–58).

Article entitled "Non–invasive pulmonary blood flow measurement by means of $CO_2$ analysis of expiratory gases" by Bosman, R.J., et al., Intensive Care Med (1991) 17:98–102.

Abstract FC 11 of article entitled "a Non–Invasive Technique for Measurement of Lung Perfusion" by H. Blomquist et al., published in "Monitoring, Computer, Instrumentation", Intensive Care Medicine (1986) 12:172.

Sackner, Marvin A., *Measurement of cardiac output by alveolar gas exchange*, Handbook of Physiology—The Respiratory System IV, Chapter 13: Pulmonary Capillary Blood Flow, pp. 233–255.

\* cited by examiner

APPARATUS AND METHOD FOR NON-INVASIVELY MEASURING CARDIAC OUTPUT

CROSS-REFERENCE TO RELATED APPLICATIONS

This application is a divisional of application Ser. No. 09/777,629, filed Feb. 6, 2001, now U.S. Pat. No. 6,648,832, issued Nov. 18, 2003, which is a continuation of application Ser. No. 09/262,510, filed Mar. 2, 1999, now U.S. Pat. No. 6,227,196, issued May 8, 2001, which is a continuation-in-part of application Ser. No. 08/770,138, filed Dec. 19, 1996, now U.S. Pat. 6,306,098, issued Oct. 23, 2001.

BACKGROUND OF THE INVENTION

1. Field of the Invention

This invention relates to non-invasive means of determining cardiac output or pulmonary capillary blood flow in patients and, more specifically, to partial re-breathing systems and methods for determining cardiac output or pulmonary capillary blood flow in patients.

2. Background of Related Art

It is important in many medical procedures to determine or monitor the cardiac output or the pulmonary capillary blood flow of a patient. Cardiac output is the volume of blood pumped by the heart over a given period of time. Pulmonary capillary blood flow is the volume of blood that participates in gas exchange in the lungs. Techniques are known and used in the art which employ the use of catheters inserted into blood vessels at certain points (e.g., into the femoral artery, the jugular vein, etc.) to monitor blood temperature and pressure and to thereby determine the cardiac output or pulmonary capillary blood flow of the patient. Although such techniques can produce a reasonably accurate result, the invasive nature of these procedures has a high potential for causing morbidity or mortality.

Adolph Fick's formula for calculating cardiac output, which was first proposed in 1870, has served as the standard by which other means of determining cardiac output and pulmonary capillary blood flow have since been evaluated. Fick's well-known equation, which is also referred to as the Fick Equation, written for carbon dioxide ($CO_2$), is:

$$Q = \frac{V_{CO_2}}{(C_{vCO_2} - C_{aCO_2})},$$

where Q is cardiac output, $V_{CO_2}$ is the amount of $CO_2$ excreted by the lungs, or "$CO_2$ elimination," and $Ca_{CO_2}$ and $Cv_{CO_2}$ are the $CO_2$ contents of arterial blood and venous blood, respectively. Notably, the Fick Equation presumes an invasive method (i.e., catheterization) of calculating cardiac output or pulmonary capillary blood flow because the arterial blood and mixed venous blood must be sampled in order to directly determine the $CO_2$ contents of arterial blood and venous blood.

It has been shown, however, that by using the principles embodied in the Fick Equation, non-invasive means may be employed to determine cardiac output or pulmonary capillary blood flow. That is, expired $CO_2$ levels, measured in terms of fraction of expired gases that comprise $CO_2$ ($f_{CO_2}$) or in terms of partial pressure of $CO_2$ ($P_{CO_2}$), can be monitored and employed to estimate the content of $CO_2$ in the arterial blood. Thus, a varied form of the Fick Equation may be employed to estimate cardiac output or pulmonary capillary blood flow based on observed changes in $f_{CO_2}$ or $P_{CO_2}$.

An exemplary use of the Fick Equation to non-invasively determine cardiac output or pulmonary capillary blood flow includes comparing a "standard" ventilation event to a change in expired $CO_2$ values and a change in excreted volume of $CO_2$, which is referred to as carbon dioxide elimination or $CO_2$ elimination ($V_{CO_2}$), which may be caused by a sudden change in ventilation. Conventionally, a sudden change in effective ventilation has been caused by having a patient inhale or breathe a volume of previously exhaled air. This technique is typically referred to as "re-breathing."

Some re-breathing techniques have used the partial pressure of end-tidal $CO_2$ ($Pet_{CO_2}$ or $et_{CO_2}$) to approximate the content of $CO_2$ in the arterial blood of a patient while the patient's lungs act as a tonometer to facilitate the measurement of the $CO_2$ content of the venous blood of the patient.

By further modification of the Fick Equation, it may be assumed that the $CO_2$ content of the patient's venous blood does not change within the time period of the perturbation. Thus, the need to directly calculate the $CO_2$ content of venous blood was eliminated by employing the so-called "partial re-breathing" method. (See, Capek et al., "Noninvasive Measurement of Cardiac Output Using Partial $CO_2$ Rebreathing," *IEEE Transactions on Biomedical Engineering*, Vol. 35, No. 9, Sep. 1988, pp. 653–661 (hereinafter "Capek").)

The carbon dioxide elimination of the patient may be non-invasively measured as the difference per breath between the volume of carbon dioxide inhaled during inspiration and the volume of carbon dioxide exhaled during expiration, and is typically calculated as the integral of the carbon dioxide signal times the rate of flow over an entire breath. The volume of carbon dioxide inhaled and exhaled may each be corrected for any deadspace or for any intrapulmonary shunt.

The partial pressure of end tidal carbon dioxide is also measured in re-breathing processes. The partial pressure of end-tidal carbon dioxide, after correcting for any deadspace, is typically assumed to be approximately equal to the partial pressure of carbon dioxide in the alveoli ($PA_{CO_2}$) of the patient or, if there is no intrapulmonary shunt, the partial pressure of carbon dioxide in the arterial blood of the patient ($Pa_{CO_2}$). Conventionally employed Fick methods of determining cardiac output or pulmonary capillary blood flow typically include a direct, invasive determination of $Cv_{CO_2}$ by analyzing a sample of the patient's mixed venous blood. The re-breathing process is typically employed to either estimate the carbon dioxide content of mixed venous blood (in total re-breathing) or to obviate the need to know the carbon dioxide content of the mixed venous blood (by partial re-breathing) or determine the partial pressure of carbon dioxide in the patient's venous blood ($Pv_{CO_2}$).

Re-breathing processes typically include the inhalation of a gas mixture that includes carbon dioxide. During re-breathing, the carbon dioxide elimination of a patient typically decreases. In total re-breathing, carbon dioxide elimination decreases to near zero. In partial re-breathing, carbon dioxide elimination does not cease. Thus, in partial re-breathing, the decrease in carbon dioxide elimination is not as large as that of total re-breathing.

Re-breathing can be conducted with a re-breathing circuit, which causes a patient to inhale a gas mixture that includes carbon dioxide. FIG. 1 schematically illustrates a conventional ventilation system that is typically used with patients who require assisted breathing during an illness, during a surgical procedure, or during recovery from a surgical procedure. The conventional ventilator system 10 includes a tubular portion 12 that may be inserted into the trachea of a patient by known intubation procedures. The end 14 (i.e., the end most distant from the patient) of the tubular portion 12 may be fitted with a Y-piece 16 that interconnects an inspiratory hose 18 and an expiratory hose 20. Both the inspiratory hose 18 and expiratory hose 20 may be connected to a ventilator machine (not shown), which delivers air into the breathing circuit through the inspiratory hose 18. A one-way valve 22 is positioned on the inspiratory hose 18 to prevent exhaled gas from entering the inspiratory hose 18 beyond the valve 22. A similar one-way valve 24 on the expiratory hose 20 limits movement of inspiratory gas into the expiratory hose 20. Exhaled air flows passively into the expiratory hose 20.

With reference to FIG. 2, an exemplary known re-breathing ventilation circuit 30 is shown. Re-breathing circuit 30 includes a tubular portion 32 insertable into the trachea of a patient by known intubation procedures. Gases may be provided to the patient from a ventilator machine (not shown) via an inspiratory hose 34 interconnected with tubular portion 32 by a Y-piece 36. Tubular portion 32 and an expiratory hose 38 are also interconnected by Y-piece 36. An additional length of hose 40 is provided in flow communication with the tubular portion 32, between the tubular portion 32 and the Y-piece 36, and acts as a deadspace for receiving exhaled gas. A three-way valve 42, generally positioned between the Y-piece 36 and the opening to the additional length of hose 40, is constructed for intermittent actuation to selectively direct the flow of gas into or from the additional length of hose 40. That is, at one setting, the valve 42 allows inspiratory gas to enter the tubular portion 32 while preventing movement of the gas into the additional length of hose 40. At a second setting, the valve 42 allows exhaled gas to enter into the expiratory hose 38 while preventing movement of gas into the additional length of hose 40. At a third setting, the three-way valve 42 directs exhaled air to enter into the additional length of hose 40 and causes the patient to re-breathe the exhaled air on the following breath to, thereby, effect re-breathing and to cause a change in the effective ventilation of the patient.

The change in $CO_2$ elimination and in the partial pressure of end-tidal $CO_2$ caused by the change in ventilation in the system of FIG. 2 can then be used to calculate the cardiac output or pulmonary capillary blood flow of the patient. Sensing and/or monitoring devices may be attached to the re-breathing ventilation circuit 30 between the additional length of hose 40 and the tubular portion 32. The sensing and/or monitoring devices may include, for example, means 44 for detecting $CO_2$ concentration and means 46 for detecting respiratory flow parameters during inhalation and exhalation. These sensing and/or monitoring devices are typically associated with data recording and display equipment (not shown). One problem encountered in use of the conventional re-breathing system is that the volume of the deadspace provided by the additional length of hose 40 is fixed and may not be adjusted. As a result, the amount of deadspace provided in the circuit for a small adult to effect re-breathing is the same amount of deadspace available for a large adult to effect re-breathing, and the resulting changes in $CO_2$ values for patients of different sizes or breathing capacities, derived from fixed-deadspace systems, can produce inadequate evaluation of a patient's cardiac output or pulmonary capillary blood flow. Further, the three-way valve 42 of the system is expensive and significantly increases the cost of the ventilation device.

During total re-breathing, the partial pressure of end-tidal carbon dioxide ($Pet_{CO_2}$) is typically assumed to be equal to the partial pressure of carbon dioxide in the venous blood ($Pv_{CO_2}$) of the patient, as well as to the partial pressure of carbon dioxide in the arterial blood ($Pa_{CO_2}$) of the patient and to the partial pressure of carbon dioxide in the alveolar blood ($PA_{CO_2}$) of the patient. The partial pressure of carbon dioxide in blood may be converted to the content of carbon dioxide in blood by means of a carbon dioxide dissociation curve.

In partial re-breathing, measurements during normal breathing and subsequent re-breathing are substituted into the carbon dioxide Fick equation. This results in a system of two equations and two unknowns (carbon dioxide content in the mixed venous blood and cardiac output), from which cardiac output or pulmonary capillary blood flow can be determined without knowing the carbon dioxide content of the mixed venous blood ($Cv_{CO_2}$).

Total re-breathing is a somewhat undesirable means of measuring cardiac output or pulmonary capillary blood flow because the patient is required to breathe directly into and from a closed volume of gases (e.g., a bag) in order to produce the necessary effect. Moreover, it is typically impossible or very difficult for sedated or unconscious patients to actively participate in inhaling and exhaling into a fixed volume.

Known partial re-breathing methods are also advantageous over invasive techniques of measuring cardiac output or pulmonary capillary blood flow because partial re-breathing techniques are non-invasive, use the accepted Fick principle of calculation, are easily automated, and facilitate the calculation of cardiac output or pulmonary capillary blood flow from commonly monitored clinical signals. However, known partial re-breathing methods are somewhat undesirable because they are a less accurate means of measuring the cardiac output or pulmonary capillary blood flow of non-intubated or spontaneously breathing patients, may only be conducted intermittently (usually at intervals of at least about four minutes), and result in an observed slight, but generally clinically insignificant, increase in arterial $CO_2$ levels. Moreover, the apparatus typically employed in partial re-breathing techniques do not compensate for differences in patient size or breathing capacities. In addition, many devices employ expensive elements, such as three-way valves, which render the devices too expensive to be used as disposable units.

Thus, there is a need for adjustable deadspace re-breathing apparatus that compensate for differences in the sizes or breathing capacities of different patients, that may be employed to provide a more accurate and continuous measurement of gases exhaled or inhaled by a patient, and are less expensive than conventional re-breathing apparatus and, thereby, facilitate use of the adjustable deadspace re-breathing apparatus as a single-use, or disposable, product. There is also a need for a more accurate method of estimating the cardiac output or pulmonary capillary blood flow of a patient.

SUMMARY OF THE INVENTION

In accordance with the present invention, apparatus and methods for measuring the cardiac output or pulmonary capillary blood flow of a patient are provided. The apparatus of the present invention includes a deadspace (i.e., volume of re-breathed gases), the volume of which can be adjusted without changing airway pressure. The invention also includes methods of adjusting the volume of deadspace to obtain a more accurate cardiac output or pulmonary capillary blood flow value. A modified form of the Fick Equation may be employed with the adjustable deadspace volume to calculate the cardiac output or pulmonary capillary blood flow of the patient. The apparatus of the present invention also employs significantly less expensive elements of construction, thereby facilitating the use of the apparatus as a disposable product.

The apparatus and methods of the present invention apply a modified Fick Equation to calculate changes in partial pressure of carbon dioxide ($P_{CO_2}$), flow, and concentration to evaluate the cardiac output or pulmonary capillary blood flow of a patient. The traditional Fick Equation, written for $CO_2$ is:

$$Q = \frac{V_{CO_2}}{(C_{v_{CO_2}} - C_{a_{CO_2}})},$$

where Q is pulmonary capillary blood flow ("PCBF"), $V_{CO_2}$ is the output of $CO_2$ from the lungs, or "$CO_2$ elimination," and $Ca_{CO_2}$ and $Cv_{CO_2}$ are the $CO_2$ contents of the arterial blood and venous blood $C_{O_2}$, respectively. It has been shown in the prior work of others that cardiac output can be estimated from calculating the change in the fraction or volume of $CO_2$ exhaled by a patient and the partial pressure of end-tidal $CO_2$ as a result of a sudden change in ventilation. That can be done by applying a differential form of the Fick Equation, as follows:

$$Q = \frac{V_{CO_{2_1}}}{(C_{v1} - C_{a1})} = \frac{V_{CO_{2_2}}}{(C_{v2} - C_{a2})},$$

where Ca is the $CO_2$ content of the arterial blood of a patient, Cv is the $CO_2$ content of the venous blood of the patient, and the subscripts 1 and 2 refer to measured values before a change in ventilation and measured values during a change in ventilation, respectively. The differential form of the Fick Equation can, therefore, be rewritten as:

$$Q = \frac{V_{CO_{2_1}} - V_{CO_{2_2}}}{(C_{v1} - C_{a1}) - (C_{v2} - C_{a2})} \text{ or } Q = \frac{\Delta V_{CO_2}}{\Delta C_{a_{CO_2}}} = \frac{\Delta V_{CO_2}}{s \Delta PetCO_2},$$

where $V_{CO_2}$ is the change in $CO_2$ elimination in response to the change in ventilation, $Ca_{CO_2}$ is the change in the $CO_2$ content of the arterial blood of the patient in response to the change in ventilation, $Pet_{CO_2}$ is the change in the partial pressure of end-tidal $CO_2$, and s is the slope of a $CO_2$ dissociation curve known in the art. The foregoing differential equation assumes that there is no appreciable change in venous $CO_2$ concentration during the re-breathing episode, as demonstrated by Capek. Also, a $CO_2$ dissociation curve, well known in the art, is used for determining $CO_2$ concentration based on partial pressure measurements.

In previous partial re-breathing methods, a deadspace, which may comprise an additional 50–250 ml capacity of air passage, was provided in the ventilation circuit to decrease the effective alveolar ventilation. In the present invention, a ventilation apparatus is provided with a deadspace having an adjustable volume to provide a change in ventilation for determining accurate changes in $CO_2$ elimination and in partial pressure of end-tidal $CO_2$ that is commensurate with the requirements of patients of different sizes or breathing capacities. In one embodiment of the ventilation apparatus, selectively adjustable deadspace is provided into which the patient may exhale and from which the patient may inhale. Thus, the adjustable deadspace volume of the apparatus accommodates a variety of patient sizes or breathing capacities (e.g., from a small adult to a large adult). As a result, the patient is provided with a volume of re-breathable gas commensurate with the patient's size or breathing capacity, which decreases the effective ventilation of the patient without changing the airway pressure of the patient. Because airway and intra-thoracic pressure are not affected by the re-breathing method of the present invention, cardiac output and pulmonary capillary blood flow are not significantly affected by re-breathing.

In an alternative method, the volume of deadspace may be effectively lessened by selectively leaking exhaled gas from the ventilation system to atmosphere or to a closed receptacle means during inspiration. Similarly, additional carbon dioxide may be introduced into the deadspace to increase the effective deadspace volume. Changing the effective deadspace volume in such a manner has substantially the same effect as changing the actual volume of the deadspace of the ventilation apparatus.

The ventilation apparatus of the present invention includes a tubular portion, which is also referred to as a conduit, to be placed in flow communication with the airway of a patient. The conduit of the ventilation apparatus may also be placed in flow communication with or include an inhalation course and an exhalation course, each of which may include tubular members or conduits. In a common configuration, the inhalation course and exhalation course may be interconnected in flow communication between a ventilator unit (i.e., a source of deliverable gas mechanically operated to assist the patient in breathing) and the patient. Alternatively, however, a ventilator unit need not be used with the ventilation apparatus. For example, inhaled air and exhaled air may be taken from or vented to atmosphere. Other conventional equipment commonly used with ventilator units or used in ventilation of a patient, such as a breathing mask, may be used with the inventive ventilation apparatus.

A pneumotachometer for measuring gas flow and a capnometer for measuring $CO_2$ partial pressure are provided along the flow path of the ventilation apparatus and, preferably, in proximity to the conduit, between the inhalation and exhalation portions of the ventilation apparatus and the patient's lungs. The pneumotachometer and capnometer detect changes in gas concentrations and flow and are preferably in electrical communication with a computer programmed (i.e., by software or embedded hardware) to store and evaluate, in substantially real time, the measurements taken by the detection apparatus. Other forms of detection apparatus may, alternatively or in combination with the pneumotachometer and the capnometer, be employed with the ventilation apparatus of the present invention.

Deadspace having an adjustable volume is provided in flow communication with the conduit. In particular, the deadspace is in flow communication with the exhalation portion of the ventilation apparatus (e.g., the expiratory course), and may be in flow communication with the inhalation portion (e.g., the inspiratory course) of the ventilation apparatus. In one embodiment, the volume of the deadspace may be manually adjusted. Alternatively, electromechanical means may be operatively associated with the computer and with the deadspace to provide automatic adjustment of the volume of the deadspace in response to the patient's size or breathing capacity or in response to changes in the ventilation or respiration of the patient.

In an alternative embodiment, a tracheal gas insufflation ("TGI") apparatus is employed to provide the change in ventilation necessary to determine pulmonary $CO_2$ changes and to determine the cardiac output or pulmonary capillary blood flow of a patient in accordance with the differential Fick Equation disclosed previously. Tracheal gas insufflation apparatus are known, and are typically used to flush the deadspace of the alveoli of the lungs and to replace the deadspace with fresh gas infused through the TGI apparatus. That is, fresh gas is introduced to the central airway of a patient to improve alveolar ventilation and/or to minimize ventilatory pressure requirements. A TGI apparatus may be interconnected, for example, by means of a catheter, with a ventilator apparatus and includes a means of introducing fresh gas into the breathing tube and into the lungs of the patient. The TGI apparatus may be used in the methods of the present invention to determine baseline measurements of $CO_2$ elimination, partial pressure of end tidal $CO_2$, or partial pressure of alveolar $CO_2$ during TGI. When the TGI system is turned off, a deadspace is formed by the patient's trachea and the endo-tracheal tube of the TGI apparatus, which facilitates measurement of a change in the partial pressure of $CO_2$ and in the amount of $CO_2$ eliminated by the patient that may be evaluated in accordance with the method of the present invention. Further, the catheter of the TGI apparatus may be variably positioned within the trachea of the patient to further adjust the deadspace volume.

During re-breathing, the deadspace provided by the apparatus of the present invention facilitates a rapid drop in $CO_2$ elimination, which thereafter increases slightly and slowly as the functional residual lung gas capacity, which is also referred to as functional residual capacity or "FRC," equilibrates with the increase in the partial pressure of $CO_2$ in the alveoli. Partial pressure of end tidal $CO_2$ increases at a slower rate than $CO_2$ elimination following the addition of deadspace, depending on alveolar deadspace and the cardiac output or pulmonary capillary blood flow of the patient, but then stabilizes to a new level. A "standard," or baseline, breathing episode is conducted for a selected period of time immediately preceding the introduction of a deadspace into the breathing circuit (i.e., immediately preceding re-breathing) and $CO_2$ elimination and partial pressure of end tidal $CO_2$ values are determined based on measurements made during the "standard" breathing event. These values are substituted as the values $V_{CO_2}$ and $Ca_{CO_2}$ in the differential Fick Equation. Carbon dioxide elimination and partial pressure of end tidal $CO_2$ values are also determined from measurements taken for a predetermined amount of time (e.g., approximately thirty seconds) following the introduction of a deadspace (i.e., after the onset of re-breathing) during partial re-breathing to provide the second set of values (subscript 2 values) in the differential Fick Equation. Thus, the predetermined amount of time at which the second set of values are obtained may be about the same as the duration of partial re-breathing. The period of time during which partial re-breathing occurs and during which normal breathing occurs may be determined by the individual patient's size and breathing capacity. Additionally, the period of time between a re-breathing episode and a subsequent normal breathing episode may vary between patients, depending on a particular patient's size and breathing capacity.

Cardiac output or pulmonary capillary blood flow may be determined in accordance with the method of the present invention by estimating the partial pressure of $CO_2$ in the alveoli or the content of the blood in capillaries that surround the alveoli of the lungs of a patient ($Cc'_{CO_2}$), or the alveolar $CO_2$ content ($CA_{CO_2}$), rather than basing the cardiac output or pulmonary capillary blood flow determination on the partial pressure of end-tidal $CO_2$, as is typically practiced in the art. Partial pressure values that are obtained from $CO_2$ measurements are converted to a value for gas content in the blood using a $CO_2$ dissociation curve or equation, as known in the art. Thus, a more accurate cardiac output or pulmonary capillary blood flow value can be determined with alveolar $CO_2$ measurements than with partial pressure of end tidal $CO_2$ measurements.

In addition, the accuracy of the cardiac output or pulmonary capillary blood flow measurement may be increased by correcting $CO_2$ elimination values to account for flow of $CO_2$ into the functional residual capacity of the lungs, which is the volume of gas that remains in the lungs at the end of expiration. The cardiac output or pulmonary capillary blood flow of the patient may then be determined by accounting for the functional residual capacity and by employing the values obtained in accordance with the method of the present invention, as well as other determined values, known values, estimated values, or any other values based on experiential data, such as by a computer processor in accordance with the programming thereof. Alternatively, cardiac output or pulmonary capillary blood flow may be estimated without accounting for functional residual capacity.

The ventilation apparatus of the present invention may also employ inexpensive yet accurate monitoring systems as compared to the systems currently used in the art. The methods of the invention may include the automatic adjustment of the deadspace volume of the apparatus to accommodate patients of different sizes or breathing capacities or changes in the ventilation or respiration of a patient, and provides consistent monitoring with modest recovery time. Further, the present apparatus and methods can be used with non-responsive, intubated patients and with non-intubated, responsive patients.

Other features and advantages of the present invention will become apparent through a consideration of the ensuing description, the accompanying drawings, and the appended claims.

DETAILED DESCRIPTION OF THE INVENTION

Ventilation Apparatus and Methods

Figure 1:
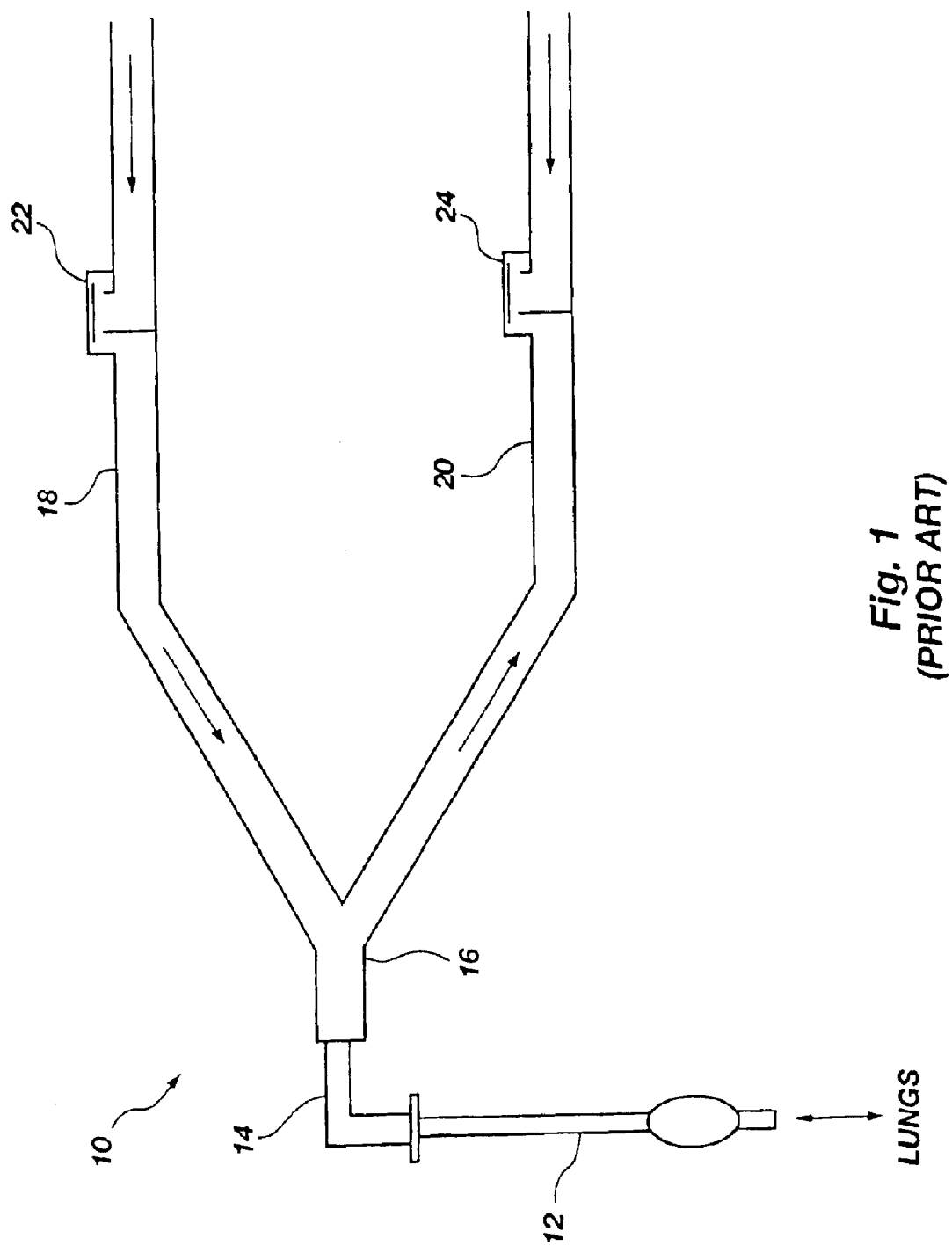
FIG. 1 is a schematic representation of a conventional ventilation system used to assist patient breathing.
Figure 2:
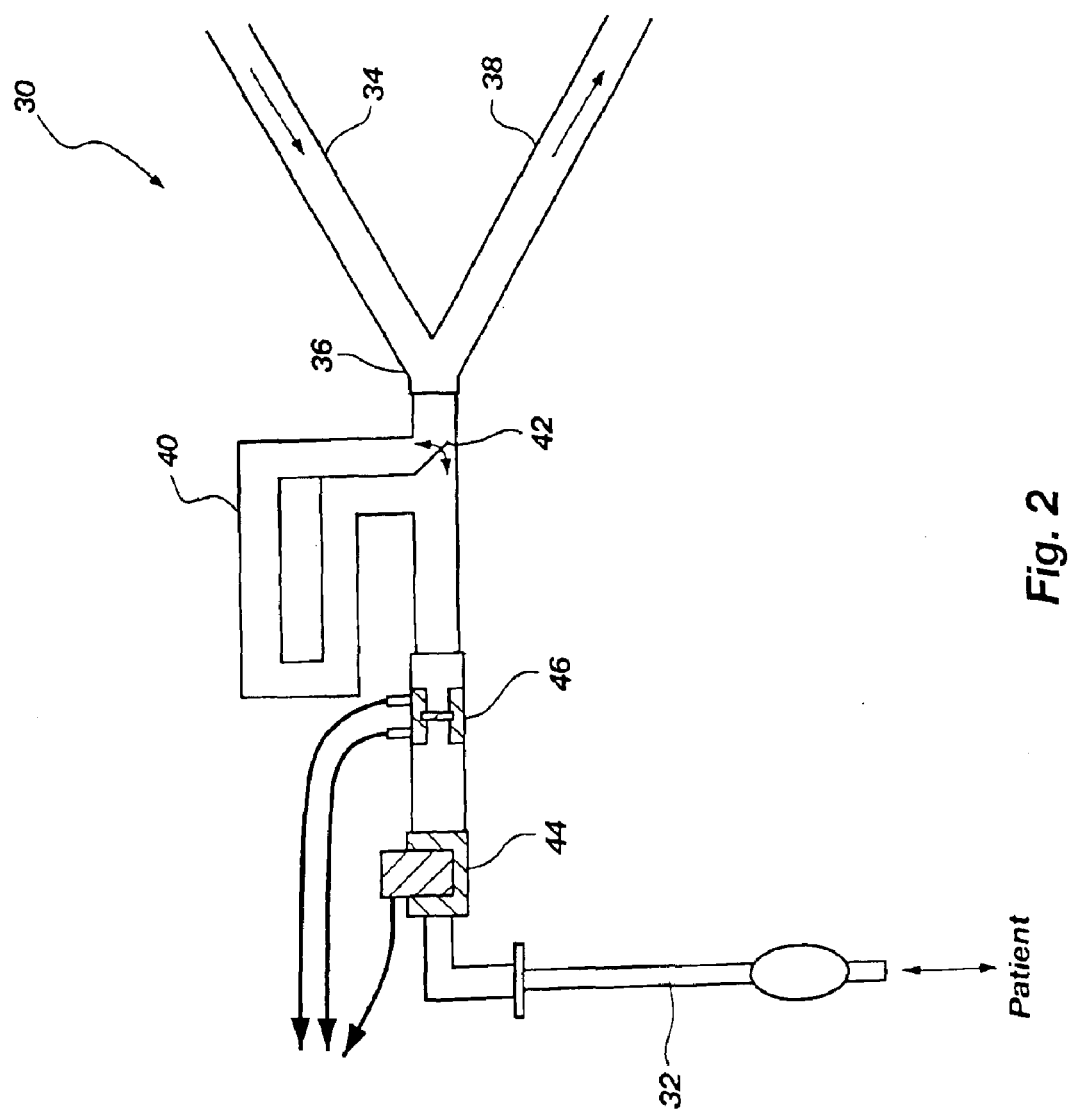
FIG. 2 is a schematic representation of a conventional re-breathing system.
Figure 3:
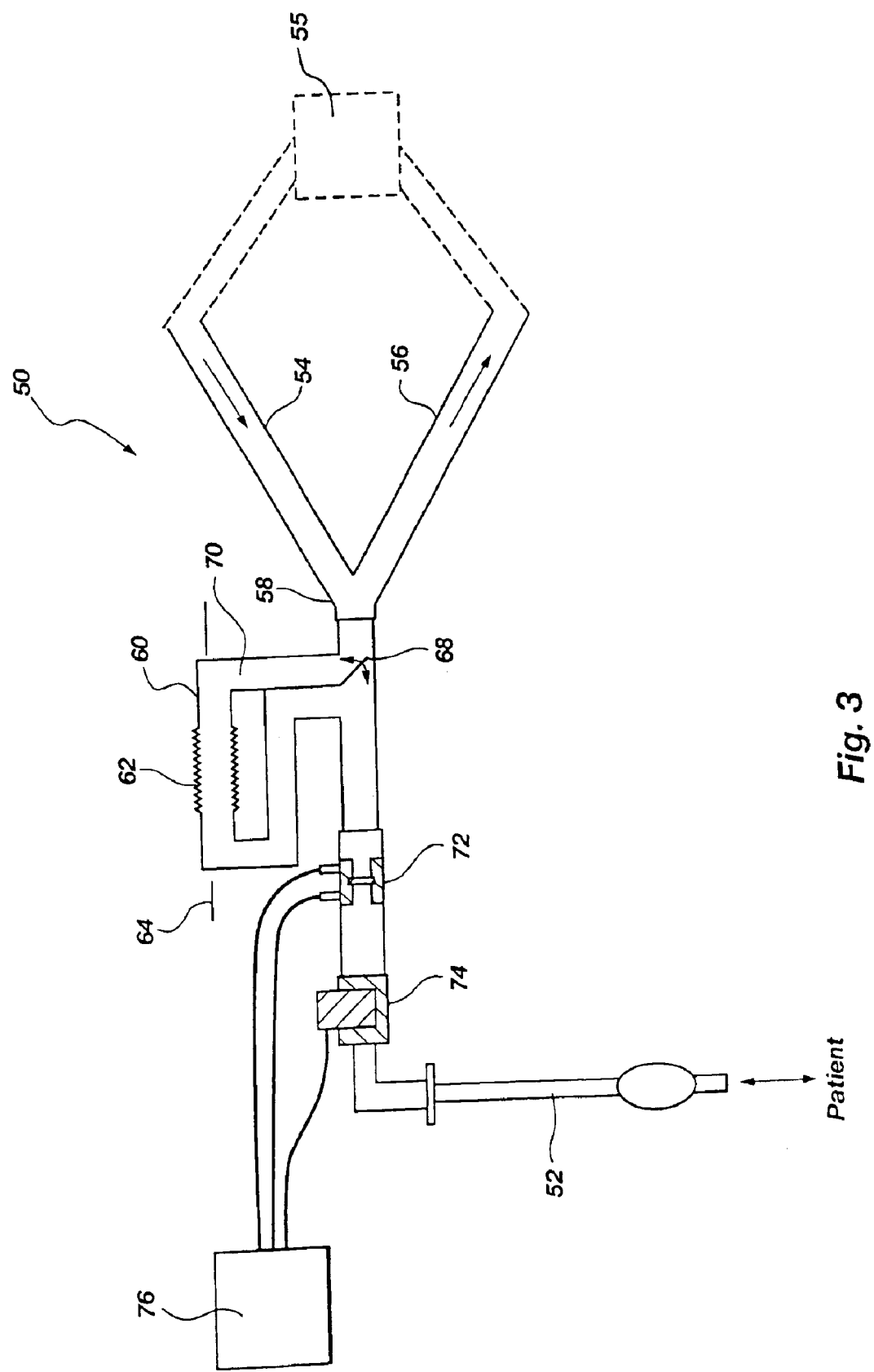
FIG. 3 is a schematic representation of a first embodiment of the ventilation apparatus of the present invention, illustrating a deadspace with an adjustably expandable volume.

FIG. 3 illustrates a breathing circuit of the present invention, which is illustrated as a ventilation apparatus 50, and which may be employed to determine the cardiac output of pulmonary capillary blood flow of a patient. Ventilation apparatus 50 comprises a tubular airway 52, which is also referred to as an airway conduit or simply as a conduit, that may be placed in flow communication with the trachea or lungs of the patient. The present ventilation apparatus 50 may be placed in flow communication with the trachea of the patient by known intubation procedures or by positioning a breathing mask over the nose and/or mouth of the patient. Ventilation apparatus 50 may be used with unconscious or uncooperative patients needing ventilation assistance, and may be used with substantially equal efficacy with patients who are conscious. Ventilation apparatus 50 may also include an inspiratory hose 54, which is also referred to as an inspiratory course or as an inspiration portion of the breathing circuit, and an expiratory hose 56, which is also referred to as an expiratory course or as an expiration portion of the breathing circuit, both of which are in substantial flow communication with tubular airway 52. The inspiratory hose 54 and the expiratory hose 56 may each be ventilated to atmosphere or operatively connected to a ventilator machine 55 to facilitate the delivery of air, breathing gases, or other breathing medium to the patient through the inspiratory hose 54. The inspiratory hose 54 and expiratory hose 56 may each be joined in flow communication with the tubular airway 52 by means of a Y-piece 58.

An additional length of conduit or hose 60, which provides a deadspace volume for receiving exhaled gas from the patient, is preferably in flow communication with the tubular airway 52. Both ends of the additional length of hose 60 are preferably in flow communication with tubular airway 52. The additional length of hose 60 is configured to be selectively expandable to readily enable the volume of deadspace to be adjusted commensurate with the size or breathing capacity of the patient, or commensurate with changes in the ventilation or respiration of the patient, such as an increased or decreased tidal volume or modified respiration rate. As suggested by FIG. 3, selective expansion of the deadspace may be accomplished by configuring the additional length of hose 60 to include an expandable section 62 made of, for example, a section of corrugated hose which can be lengthened or shortened by simply pulling or pushing the expandable section 62 substantially along its longitudinal axis 64. The section of corrugated hose will preferably retain the length to which it is set until adjusted again. Other suitable means of providing adjustable expansion of the volume of the deadspace and, thus, methods of adjusting the volume of the deadspace of the breathing circuit are also available and within the scope of the present invention.

A three-way valve 68 may be disposed along the flow path of tubular airway 52 between the two ends of additional length of hose 60 and selectively positioned to direct inspiratory gas into a deadspace 70 comprised of the additional length of hose 60 upon inhalation, to selectively prevent exhaled gas from entering the deadspace 70 during normal breathing, or to direct exhaled gas into deadspace 70 during re-breathing so that the patient will re-breathe previously exhaled gases or a gas including $CO_2$ from the deadspace 70.

A flow meter 72, such as a pneumotachometer, and a carbon dioxide sensor 74, which is typically referred to as a capnometer, may be exposed to the flow path of the ventilation apparatus, preferably between the tubular airway 52 and the additional length of hose 60. Thus, the flow meter 72 and carbon dioxide sensor 74 are exposed to any air or gas that flows through ventilation apparatus 50. The flow meter 72 detects gas flow through the ventilation apparatus 50.

A flow meter 72 of a known type, such as the differential-pressure type respiratory flow sensors manufactured by Novametrix Medical Systems Inc. ("Novametrix") of Wallingford, Conn. (e.g., the Pediatric/Adult Flow Sensor (Catalog No. 6717) or the Neonatal Flow Sensor (Catalog No. 6718)), which may be operatively attached to a ventilation apparatus (not shown), as well as respiratory flow sensors based on other operating principles and manufactured or marketed by others, may be employed to measure the flow rates of the breathing of the patient.

The carbon dioxide sensor 74 detects $CO_2$ levels and, therefore, facilitates a determination of changes in $CO_2$ levels that result from changes in the ventilation or respiration of the patient. The carbon dioxide sensor 74 and its associated airway adapter may be an "on airway" sensor, a sampling sensor of the type which withdraws a side stream sample of gas for testing, or any other suitable type of carbon dioxide sensor. Exemplary carbon dioxide sensors and complementary airway adapter include, without limitation, the Pediatric/Adult Single Patient Use Airway Adapter (Catalog No. 6063), the Pediatric/Adult Reusable Airway Adapter (Catalog No. 7007), or the Neonatal/Pediatric Reusable Airway Adapter (Catalog No. 7053), which are manufactured by Novametrix. Alternatively, combined flow and carbon dioxide sensors, as known in the art, may be employed.

The data obtained by the flow meter 72 and by the carbon dioxide sensor 74 are preferably used to determine the cardiac output or pulmonary capillary blood flow of the patient. Accordingly, the flow meter 72 and carbon dioxide sensor 74 may be operatively associated with a computer 76 (e.g., by direct cable connection, wireless connection, etc.) programmed to store or analyze data from the flow meter 72 and the carbon dioxide sensor 74 and programmed to determine the cardiac output or pulmonary capillary blood flow of the patient from the stored or analyzed data.

As previously described herein, the differential Fick Equation requires a change in the partial pressure of carbon dioxide and a change in carbon dioxide elimination to be induced in the patient in order to estimate the cardiac output or pulmonary capillary blood flow of the patient. As the patient re-breathes previously exhaled gas, the amount of $CO_2$ inhaled by the patient increases, thereby facilitating the evaluation of increased $CO_2$ levels during a change in effective ventilation, as compared to the $CO_2$ levels of the patient's breathing during normal ventilation. The re-breathing ventilation apparatus 50 of the present invention provides the ability to selectively adjust the volume of deadspace from which air is re-breathed in accordance with the size or breathing capacity of the patient, or in response to changes in the ventilation or respiration of the patient. For example, if the detected change in partial pressure of end tidal $CO_2$ is less than a threshold pressure (e.g., 1 mm Hg), or the change in $CO_2$ elimination is less than a threshold percentage or fraction (e.g., 20% or 0.2) of a baseline $CO_2$ elimination, then the deadspace volume may be increased by an appropriate amount (e.g., 20%). Similarly, if the detected change in partial pressure of end tidal $CO_2$ is greater than a threshold pressure (e.g., 12 mm Hg), or the change in $CO_2$ elimination is greater than a threshold percentage or fraction (e.g., 80% or 0.8) of the baseline $CO_2$ elimination, then the deadspace volume may be decreased by an appropriate amount (e.g., 20%).

Figure 4:
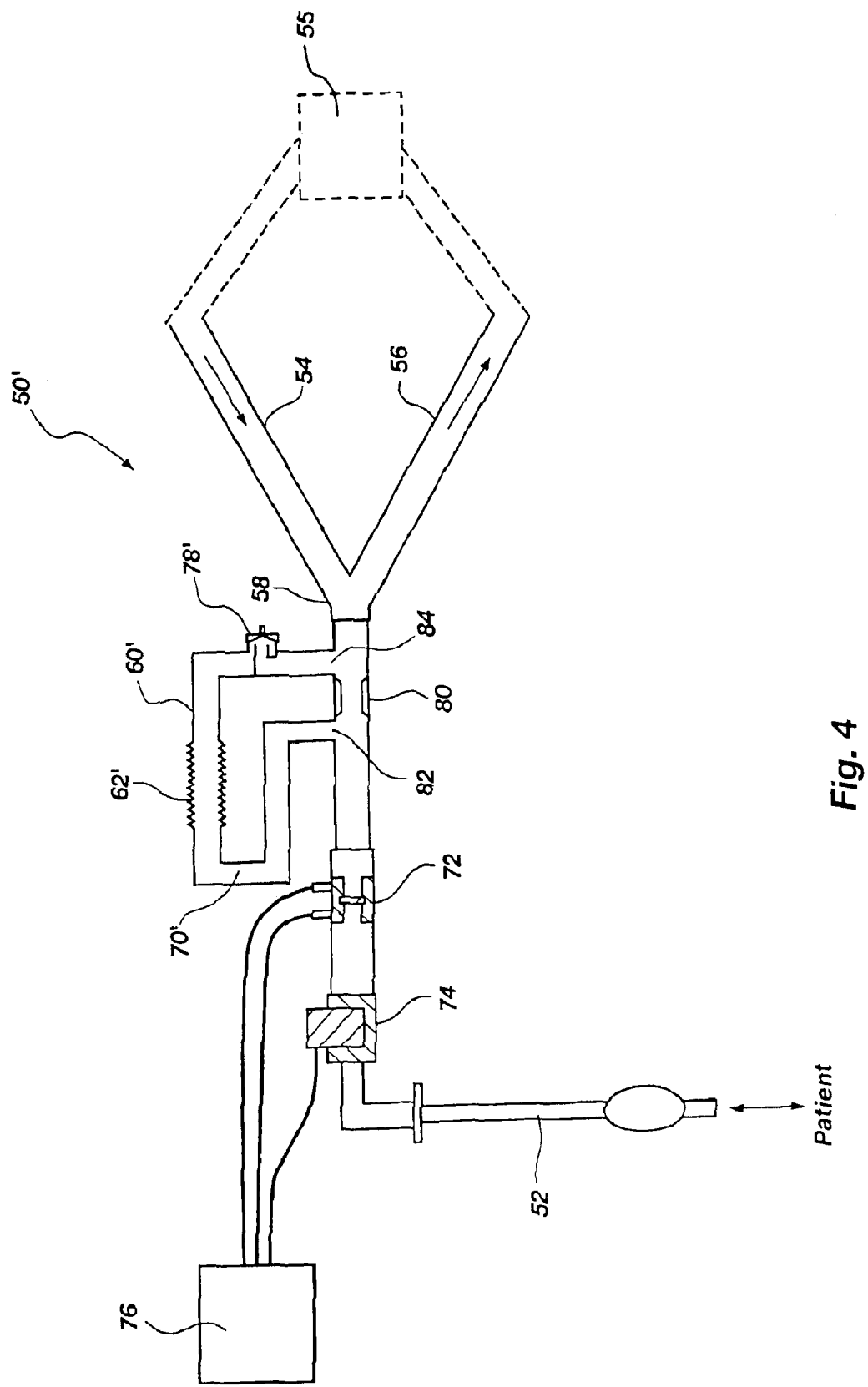
FIG. 4 is a schematic representation of an alternative embodiment of the present invention, wherein the re-breathing circuit is constructed with an evacuation valve.

In an alternative embodiment of the re-breathing ventilation apparatus 50' of the invention, as shown in FIG. 4, the expense of using a three-way valve may be eliminated by disposing an inexpensive two-way valve 78' along the flow path of the additional length of hose 60' and by positioning a flow restrictor 80 (e.g., a region of tubular airway 52 of decreased inner diameter) along tubular airway 52 between the inlet 82 and outlet 84 (i.e., the two ends) of the additional length of hose 60'. Thus, when the two-way valve 78' is closed, inhaled and exhaled gases will be directed through the flow restrictor 80. During re-breathing, the two-way valve 78' is placed in an open position so that the exhaled air, encountering the flow restrictor 80, follows the course of less resistance into the deadspace 70'. Inhaled, re-breathed air similarly follows the course of least resistance and flows from the deadspace 70'. As the optimal amount of air re-breathed by the patient may depend upon the size, breathing capacity, or changes in the ventilation or respiration of the patient, or on another factor, it may be desirable to adjust the deadspace 70' at the expandable section 62' to provide the necessary volume of deadspace for determining the cardiac output or pulmonary capillary blood flow of the patient.

Figure 5C:
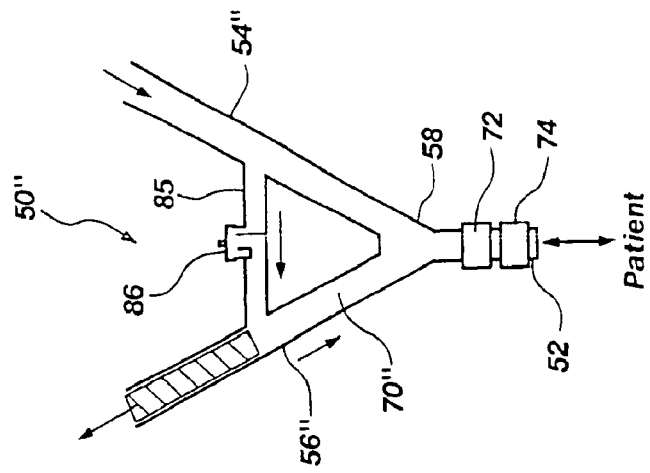
FIGS. 5A–5C are schematic representations of another alternative embodiment of the present invention, wherein the inspiratory course and expiratory course of the breathing circuit are interconnected and the breathing circuit includes a two-way valve closeable across a flow path of the breathing circuit.
Figure 5B:
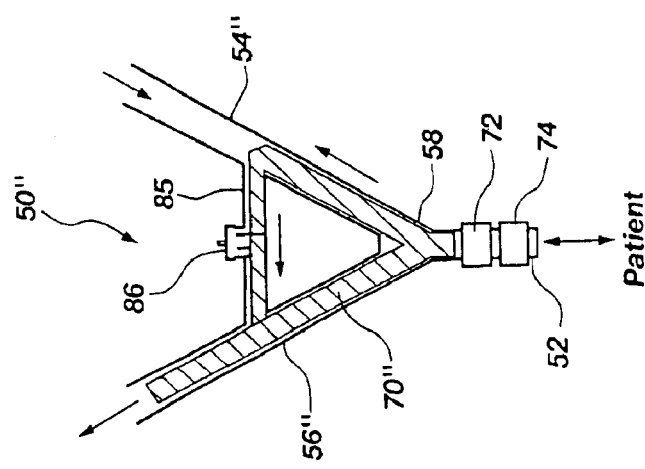
Figure 5A:
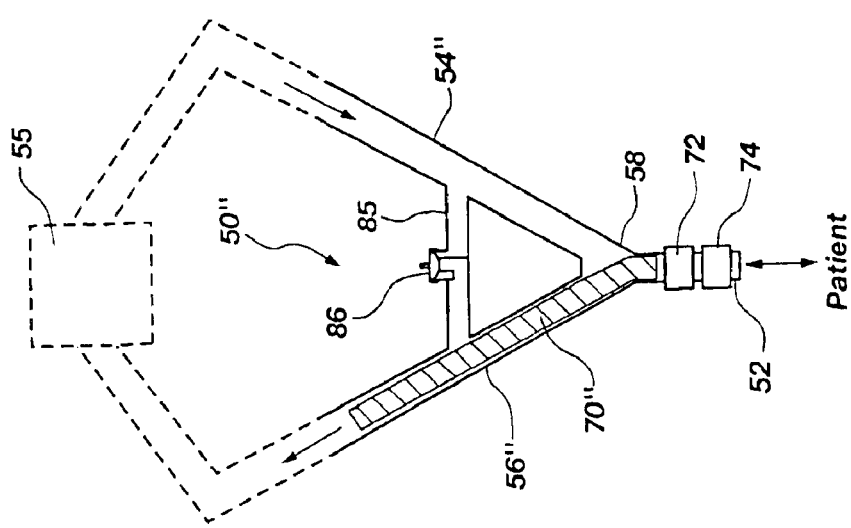

In another alternative embodiment of the ventilation apparatus 50" of the present invention, as shown in FIGS. 5A–5C, a shunt line 85 is positioned between the inspiratory course 54" and the expiratory course 56" to provide a selectively-sized deadspace 70" in the re-breathing circuit. In the configuration of the embodiment shown in FIGS. 5A–5C, the inspiratory course 54" and expiratory course 56" may comprise at least a part of the deadspace 70". A two-way shunt valve 86, positioned in the flow path of the shunt line 85, selectively directs the flow of inspired and expired gas, dependent upon whether the shunt valve 86 is placed in an open position or a closed position. Thus, when the ventilation apparatus 50" is configured for normal or baseline breathing, as depicted in FIG. 5A, exhaled air (represented by the shaded area) will enter the expiratory course 56". During normal breathing, the shunt valve 86 is placed in the closed position. During a re-breathing episode, as depicted in FIG. 5B, the shunt valve 86 is placed in the open position, and exhaled gas may fill a portion of the inspiratory course 54", substantially all of the expiratory course 56", and the shunt line 85, all of which serve as the deadspace 70".

Figure 6:
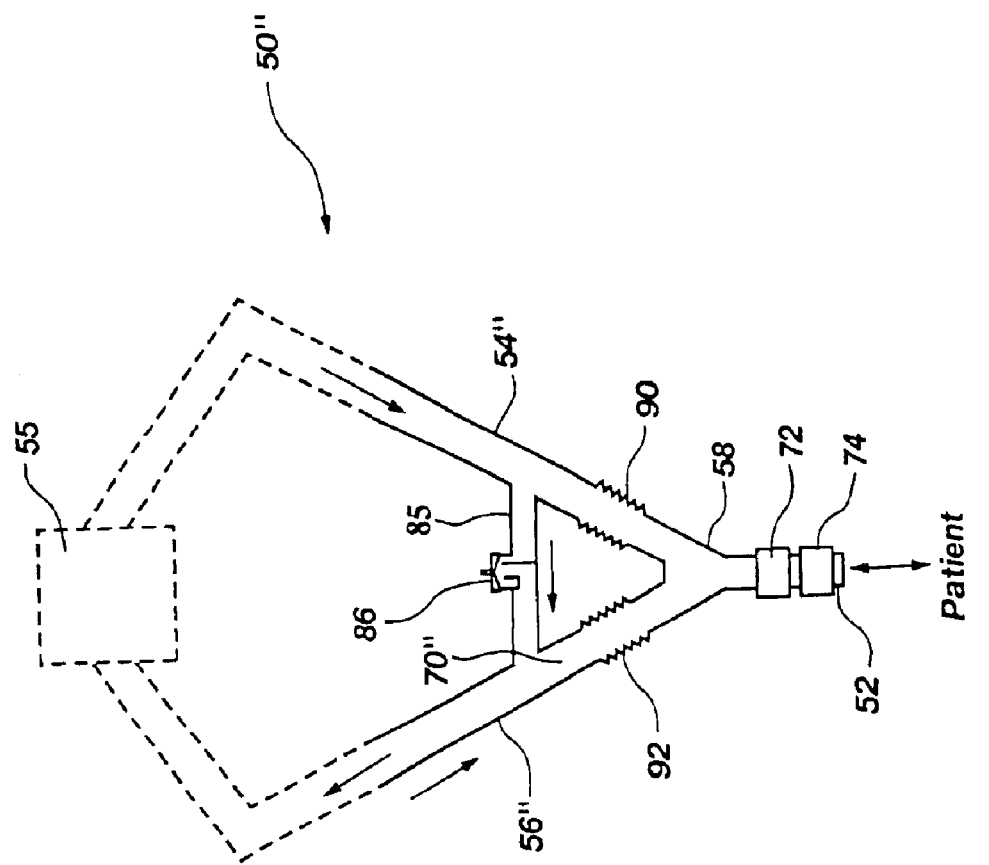
FIG. 6 is a schematic representation of an alternative embodiment similar to the embodiment shown in FIGS. 5A–5C, wherein the volumes of the inspiratory course and expiratory course of the breathing circuit are adjustably expandable.

The deadspace 70" in the embodiment shown in FIGS. 5A–5C may be rendered further expandable, as shown in FIG. 6, by structuring the inspiratory course 54" with an expandable section 90 positioned between the shunt line 85 and the Y-piece 58, and/or by structuring the expiratory course 56" with an expandable section 92 positioned between the shunt line 85 and the Y-piece 58. Thus, the deadspace 70" can be selectively adjusted in accordance with the size or capacity of the patient, or responsive to operating conditions, by increasing or decreasing the volume of the expandable sections 90, 92 of the inspiratory course 54" and expiratory course 56", respectively. Shunt line 85 may similarly include a volume expandable section. As explained previously in reference to FIG. 3, any suitable adjustably expandable means may be employed as expandable sections 90, 92. For example, as depicted in FIG. 6, the expandable sections 90, 92 may be fabricated from a corrugated plastic material, the length of which can be easily expanded or contracted and preferably substantially maintained until re-adjusted. The embodiment of FIG. 6 provides a particularly simple and inexpensive construction that may render it easy-to-use and facilitate its use as a disposable product.

Figure 7:
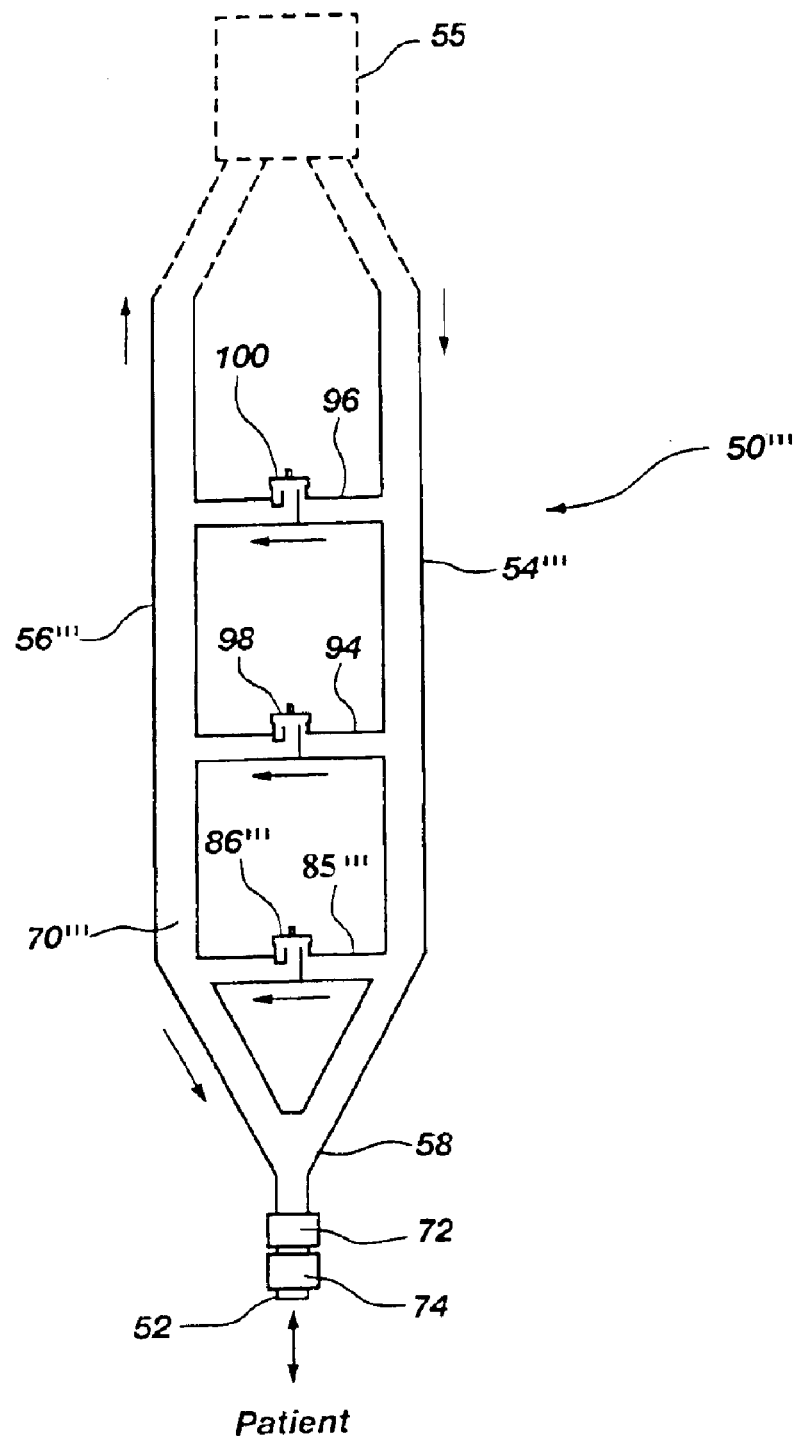
FIG. 7 is a schematic representation of another embodiment of the invention, wherein a series of valves is provided along the length of the inspiratory course and expiratory course of the breathing circuit to provide a selectable volume of deadspace dependent upon the size, breathing capacity, or changes in the ventilation or respiration of the patient.

In yet another embodiment of the ventilation apparatus 50''' of the present invention, as shown in FIG. 7, a plurality of shunt lines 85''', 94, 96 is positioned between the inspiratory course 54''' and the expiratory course 56''', with each shunt line 85''', 94, 96 including a two-way shunt valve 86''', 98, 100, respectively, disposed along the flow path thereof. In operation, the amount of deadspace 70''' desired, according to the size or breathing capacity of the patient or other factors, may be selectively adjusted by permitting exhaled gas to move through any suitable combination of shunt lines 85''', 94, 96. For example, given a patient of average size or lung capacity, it may be appropriate to use shunt line 85''' and shunt line 94 as potential deadspace 70'''. Thus, as the patient exhales in a re-breathing episode, the shunt valves 86''', 98 associated with shunt line 85''' and shunt line 94, respectively, may be placed in an open position to permit exhaled and re-breathable gas to fill the expiratory course 56''', the inspiratory course 54''' between shunt line 94 and the Y-piece 58, shunt line 85''', and shunt line 94. With a patient of larger size or greater lung capacity, it may be necessary to use the third shunt line 96 to provide sufficient deadspace 70''' for re-breathing. Notably, each shunt valve 86''', 98, 100 may be in electromechanical communication with the computer 76 (see FIG. 3) so that the computer may determine, from the carbon dioxide sensor 74 (see FIG. 3), for example, that a different volume of deadspace 70''' is needed. The computer 76 may then direct the opening or closing of one or more of the shunt valves 86''', 98, 100 to provide a sufficient volume of deadspace 70'''.

Figure 12:
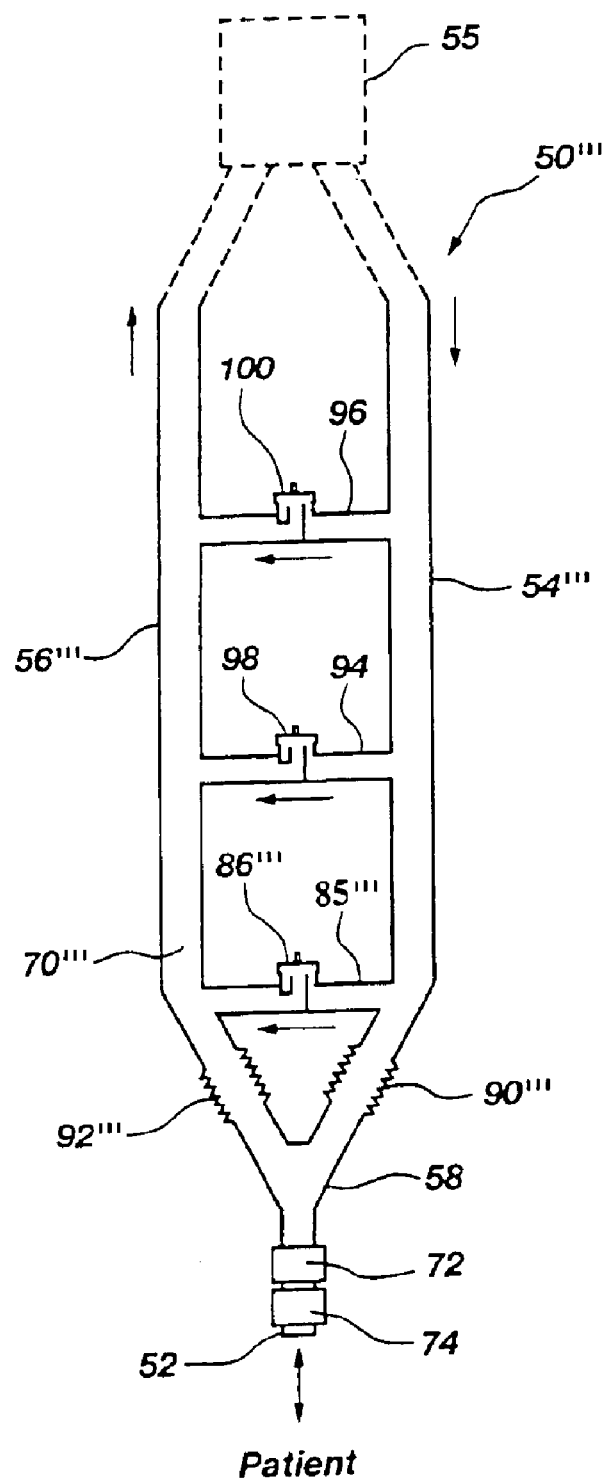
FIG. 12 is a schematic representation of a variation of the ventilation apparatus of FIG. 7, including sections having selectively expandable volumes.

Referring to FIG. 12, as a variation of the embodiment illustrated in FIG. 7, the ventilation apparatus 50''' may also include selectively expandable sections 90''', 92''' similar to those shown in FIG. 6. Although expandable sections 90''' and 92''' are illustrated as being disposed along inspiratory course 54''' and expiratory course 56''', sections of expandable volume may also be disposed along other portions of the potential deadspace of the breathing circuit, such as along any of shunt lines 85''', 94, or 96.

Figure 8A:
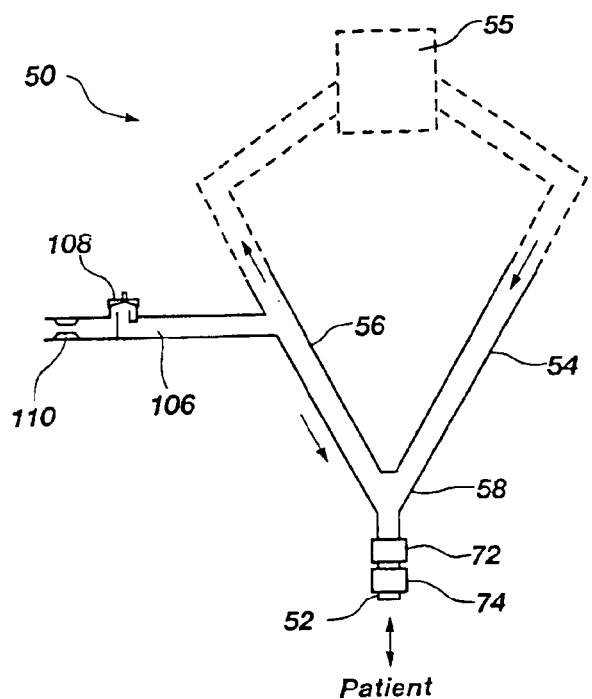
FIGS. 8A and 8B are schematic representations of another embodiment of the invention, wherein an evacuation valve is provided with a vent to atmosphere and to a receptacle or chamber, respectively.

In the several embodiments of the invention previously illustrated and described, the amount or volume of the deadspace has been selectively adjustable by providing means for adjusting the volume of the deadspace, such as by providing length-expanding means. It may be equally appropriate, however, to provide a change in ventilation, as required by the differential Fick Equation, by leaking some of the exhaled gas out of the system during the inspiration phase of a breath or by increasing the level of $CO_2$ in the deadspace, both of which provide an effective change in the volume of deadspace. Thus, as illustrated by FIG. 8A, the ventilation apparatus 50 of the present invention may include an evacuation element or component. The evacuation element may include an evacuation line 106 in flow communication with at least the expiratory course 56 of the ventilation apparatus 50. The evacuation element includes a structure that permits gas or another breathing medium to flow into or out of the ventilation apparatus 50, such as an evacuation valve 108, which is also referred to as a valve, that, when opened, allows exhaled gas to escape the ventilation apparatus 50 through an orifice 110 positioned at the end of the evacuation line 106 or permits gas to be introduced into the ventilation apparatus 50. Alternatively, a valve may be positioned in flow communication with ventilation apparatus 50 to facilitate the flow of gases therefrom.

The volume of exhaled gas that should be leaked from the ventilation apparatus 50 or introduced therein during a re-breathing event, as well as the timing and duration of such leakage or introduction, may be determined by the computer 76 (see FIG. 3) in response to flow conditions, $CO_2$ conditions, the size or breathing capacity of the patient, or changes in the ventilation or breathing of the patient. In addition, the evacuation valve 108, which may be in electromechanical communication with the computer 76, may be selectively actuated by the computer 76 in accordance with the flow conditions, the $CO_2$ conditions, the size or breathing capacity of the patient, or changes in the ventilation or respiration of the patient.

Figure 8B:
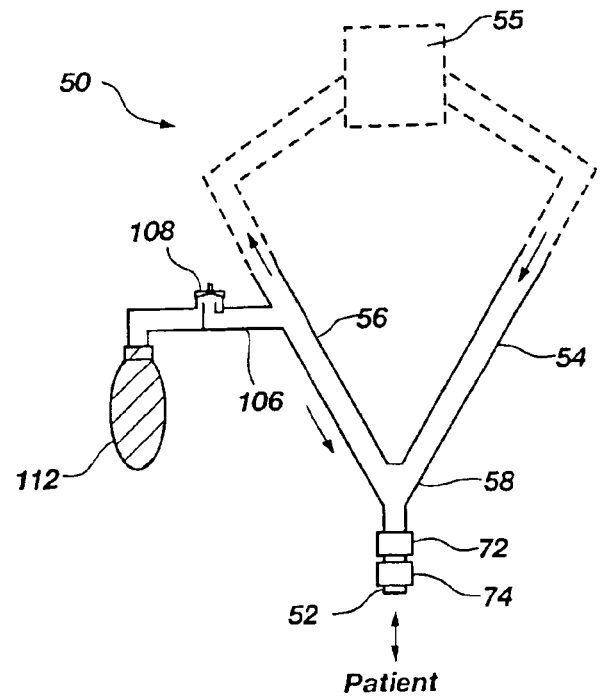

With reference to FIG. 8B, where a patient is anesthetized or is otherwise exhaling gas which is undesirable for venting to the atmosphere, a chamber or receptacle 112, such as an expandable bag, may be disposed along the evacuation line 106 or otherwise in flow communication with the evacuation valve 108 to receive the exhaled gas leaked from the ventilation apparatus.

Figure 9:
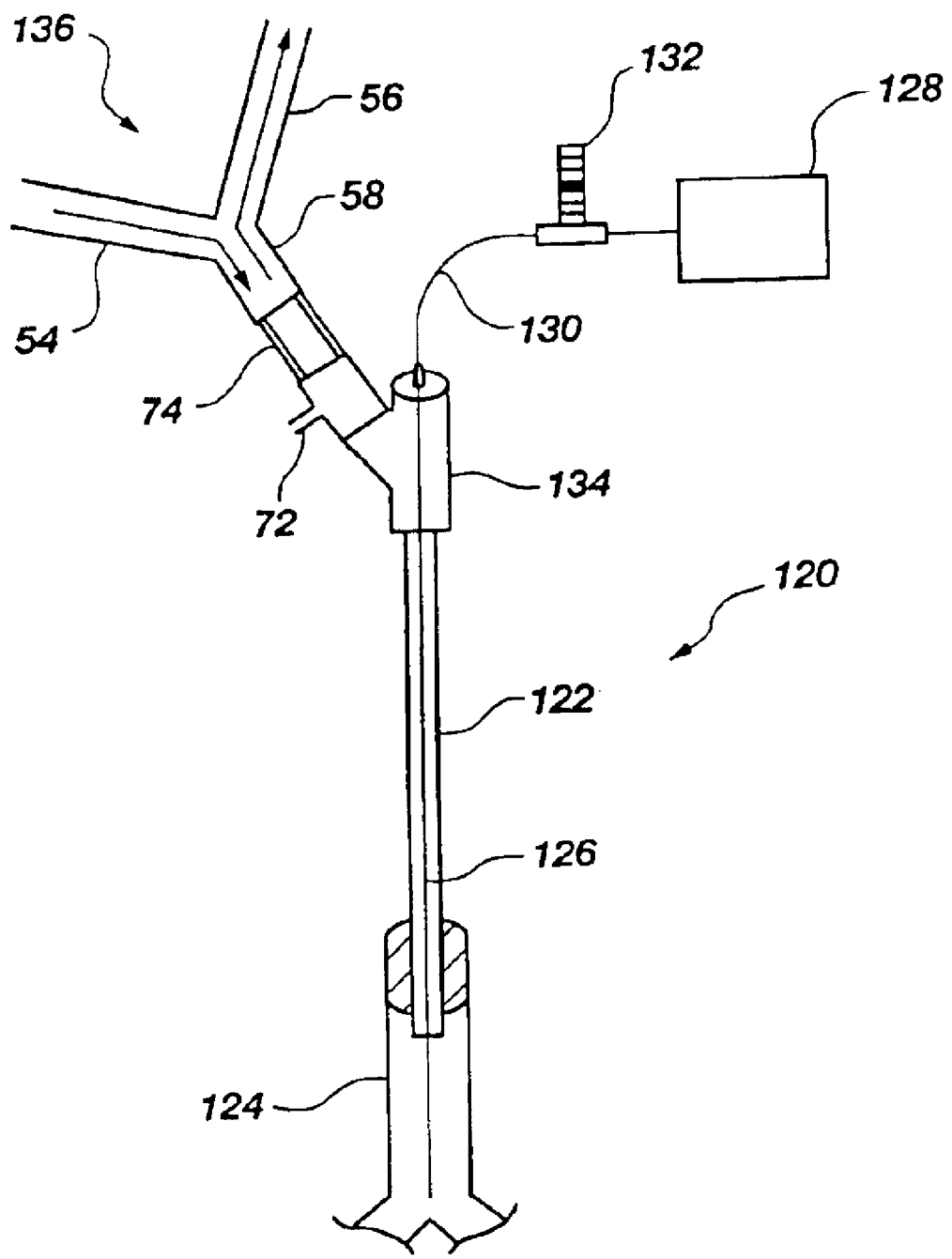
FIG. 9 is a schematic representation of a breathing circuit of the present invention that includes a tracheal gas insufflation apparatus, which can be used to provide a volume of deadspace.

FIG. 9 schematically illustrates the use of a tracheal gas insufflation (TGI) apparatus 120 to provide the necessary deadspace in determining the cardiac output or pulmonary capillary blood flow of a patient. TGI apparatus 120 are typically used to ventilate sick patients who require the injection of fresh gas into their central airway to improve alveolar ventilation. TGI apparatus can be configured to provide continuous or phasic (e.g., only during inhalation) injections of gas. The TGI apparatus supplies gas, or an oxygen/gas mixture, to the lungs with every breath. As shown in FIG. 9, the TGI apparatus comprises an endotracheal tube 122, which may be inserted into the trachea 124 of the patient by known intubation procedures. A catheter 126 extends through the endotracheal tube 122 and into the patient's lungs, typically just above the carina. Gas or an oxygen/gas blend is provided from a gas source 128 and is directed through gas delivery tubing 130 into the catheter 126. A flow meter 132 disposed along gas delivery tubing 130 and in flow communication therewith may assist in determining the optimum amount of gas to be introduced into the lungs.

An adaptor fitting 134 may be used to connect a ventilation apparatus 136, such as the type previously described in reference to FIGS. 1–8(B), to the TGI apparatus 120. That is, the ventilation apparatus 136 may include a Y-piece 58 from which an inspiratory course 54 and an expiratory course 56 extend. The ventilation apparatus 136 may also include a flow meter 72 and a carbon dioxide sensor 74 disposed in flow communication therewith to collect data during normal breathing and during a re-breathing event. In the illustrated TGI apparatus 120, the endotracheal tube 122 provides a volume of deadspace that may be required for re-breathing in addition to any deadspace volume provided by the ventilation apparatus 136. In order to act as a deadspace, however, the TGI apparatus (i.e., the gas source 128 and flow meter 132) is preferably turned off, the amount of insufflation reduced, or the TGI apparatus otherwise disabled. Exhaled air is thereby allowed to flow into the endotracheal tube 122 and, preferably, through the Y-piece 58. The endotracheal tube 122 and ventilation apparatus 136 or portions thereof may then serve as deadspace. The volume of deadspace provided by the TGI apparatus 120 may be further increased or decreased, as necessary, by varying the depth to which the catheter 126 is positioned in the patient's trachea.

A computer 76 (see FIG. 3) to which the flow meter 72 and the carbon dioxide sensor 74 may be connected can be programmed to receive data from the flow meter 72 and the carbon dioxide sensor 74 and to analyze the data to determine or estimate the cardiac output or pulmonary capillary blood flow of the patient.

Methods of Determining Cardiac Output or Pulmonary Capillary Blood Flow

The determination of cardiac output or pulmonary capillary blood flow for a given patient may be based on data obtained with the flow monitor and the carbon dioxide sensor that are associated with the ventilation apparatus of the present invention. Raw flow and $CO_2$ signals from the flow monitor and the carbon dioxide sensor may be filtered to remove any artifacts, and the flow signals and $CO_2$ signals (e.g., data regarding partial pressure of $CO_2$) may be stored by the computer 76.

Each breath, or breathing cycle, of the patient may be delineated, as known in the art, such as by continually monitoring the flow rate of the breathing of the patient.

For each breathing cycle, the partial pressure of end-tidal $CO_2$, carbon dioxide elimination ($V_{CO_2}$), the fraction of inspired, or "mixed inspired," $CO_2$, and the airway deadspace are calculated. End-tidal $CO_2$ is measured, as known in the art. Carbon dioxide elimination is typically calculated as the integral of the respiratory flow over a breathing cycle (in milliliters) multiplied by the fraction of $CO_2$ over the entire breath. The fraction of inspired $CO_2$ is the integral of $CO_2$ fraction times the air flow during inspiration, divided by the volume (in milliliters) of inspired gas.

The values of $V_{CO_2}$ and $Pet_{CO_2}$ may be filtered by employing a median filter, which uses a median value from the most recent value of recorded $V_{CO_2}$ and $Pet_{CO_2}$ values and the two values that precede the most recent measured value, as known in the art.

Figure 10:
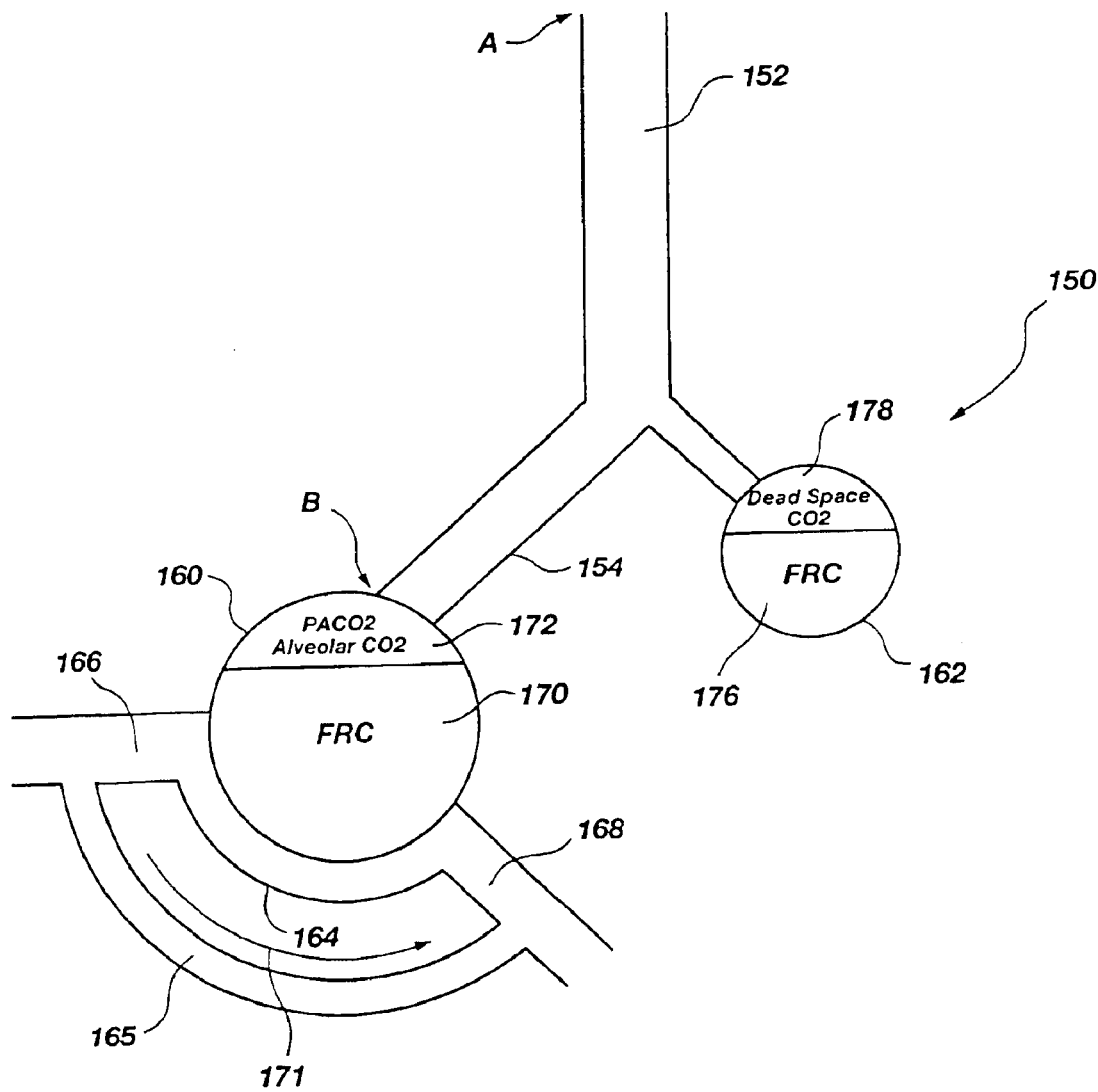
FIG. 10 is a schematic representation of human lungs, illustrating the concepts of parallel deadspace, alveolar deadspace and serial deadspace in the lungs of a patient.

Preferably, when calculating $V_{CO_2}$, the $V_{CO_2}$ value is corrected to account for anatomic deadspace and alveolar deadspace. With reference to FIG. 10, the lungs 150 of a patient may be described as including a trachea 152, two bronchi 154 and numerous alveoli 160, 162. The anatomic, or "serial," deadspace of lungs 150 includes the volume of the trachea 152, bronchi 154, and other components of lungs 150 which hold gases, but do not participate in gas exchange. The anatomic deadspace exists approximately in the region located between arrows A and B. The so-called "shunted" blood bypasses pulmonary capillaries by way of an intrapulmonary shunt 165.

Lungs 150 typically include alveoli 160 that are in contact with blood flow and which can facilitate oxygenation of the blood, which are referred to as "perfused" alveoli, as well as unperfused alveoli 162. Both perfused alveoli 160 and unperfused alveoli 162 may be ventilated. The volume of unperfused alveoli is the alveolar deadspace.

Perfused alveoli 160 are surrounded by and in contact with pulmonary capillaries 164. As deoxygenated blood 166 enters pulmonary capillaries 164, oxygen binds to the hemoglobin molecules of the red blood cells of the blood, and $CO_2$ is released from the hemoglobin. Blood that exits pulmonary capillaries 164 in the direction of arrow 171 is referred to as oxygenated blood 168. In alveoli 160 and 162, a volume of gas known as the functional residual capacity (FRC) 170 remains following exhalation. The alveolar $CO_2$ is expired from a portion 172 of each of the alveoli 160 that is evacuated, or ventilated, during exhalation.

The ventilated portion 178 of each of the unperfused alveoli 162 may also include $CO_2$. The $CO_2$ of ventilated portion 178 of each of the unperfused alveoli 162, however, is not the result of $O_2$ and $CO_2$ exchange in that alveolus. Since the ventilated portion 178 of each of the unperfused alveoli 162 is ventilated in parallel with the perfused alveoli, ventilated portion 178 is typically referred to as "parallel" deadspace (PDS). Unperfused alveoli 162 also include a FRC 176, which includes a volume of gas that is not evacuated during a breath.

In calculating the partial pressure of $CO_2$ in the alveoli ($PA_{CO_2}$) of the patient, the FRC and the partial pressure of $CO_2$ in the parallel deadspace in each of the unperfused alveoli 162 is preferably accounted for. FRC may be estimated as a function of body weight and of the airway deadspace volume by the following equation:

$$FRC = FRC\text{-factor} \cdot (\text{airway deadspace} + \text{offset value}),$$

where FRC-factor is either an experimentally determined value or is based on published data (e.g., "experiential" data) known in the art, and the offset value is a fixed constant which compensates for breathing masks or other equipment components that may add deadspace to the breathing circuit and, thereby, unacceptably skew the relationship between FRC and deadspace.

The partial pressure of $CO_2$ in the parallel deadspace ($CO_{2\ PDS}$) may be calculated from the mixed inspired $CO_2$ ($Vi_{CO_2}$) added to the product of the serial deadspace multiplied by the end tidal $CO_2$ of the previous breath ($Pet_{CO_2}(n-1)$). Because the average partial pressure of $CO_2$ in the parallel deadspace is equal to the partial pressure of $CO_2$ in the parallel deadspace divided by the tidal volume ($V_t$) (i.e., the total volume of one respiratory cycle, or breath), the partial pressure of $CO_2$ in the parallel deadspace may be calculated on a breath-by-breath basis, as follows:

$$P_{CO_2\ PDS}(n) = [FRC/(FRC+V_t)] \cdot P_{CO_2\ PDS}(n-1) + (P_{bar} \cdot (([Vi_{CO_2} + \text{deadspace} \cdot Pet_{CO_2}(n-1)/P_{bar})]/V_t) \cdot [V_t/(V_t+FRC)])),$$

where (n) indicates a respiratory profile parameter (in this case, the partial pressure of $CO_2$ in the parallel deadspace, $P_{CO_2\ PDS}(n)$) from the most recent breath and (n−1) indicates a respiratory profile parameter from the previous breath.

The partial pressure of end-tidal $CO_2$, which is assumed to be substantially equal to a weighted average of the partial pressure of $CO_2$ in all of the perfused and unperfused alveoli of a patient, may be calculated as follows:

$$Pet_{CO_2} = \circledR(r)PA_{CO_2} + (1-r)P_{CO_2\ PDS},$$

where r is the perfusion ratio, which is calculated as the ratio of perfused alveolar ventilation to the total alveolar ventilation, or $(V_A - V_{PDS})/V_A$. The perfusion ratio may be assumed to be about 0.95 or estimated, as known in the art. Alternatively, the perfusion ratio may be determined by comparing arterial $P_{CO_2}$, which measurement may be obtained directly from arterial blood and assumed to be substantially the same as alveolar $P_{CO_2}$, to end tidal $P_{CO_2}$ values by rearranging the previous equation as follows:

$$r = (Pet_{CO_2} - P_{CO_2 PDS})/(PA_{CO_2} - P_{CO_2\ PDS}).$$

By rearranging the preceding $Pet_{CO_2}$ equation, the alveolar $CO_2$ partial pressure of the patient may be calculated. Preferably, alveolar $CO_2$ partial pressure is calculated from the end-tidal $CO_2$ and the $CO_2$ in the parallel deadspace, as follows:

$$PA_{CO_2} = [Pet_{CO_2} - (1-r)P_{CO_2\ PDS}]/r.$$

The alveolar $CO_2$ partial pressure may then be converted to alveolar blood $CO_2$ content ($CA_{CO_2}$) using an equation, such as the following:

$$CA_{CO_2} = (6.957 \cdot Hb_{conc} + 94.864) \cdot ln(1 + 0.1933(PA_{CO_2})),$$

where $CA_{CO_2}$ is the content of $CO_2$ in the alveolar blood and Hb is the concentration of hemoglobin in the blood of the pulmonary capillaries. J. M. Capek and R. J. Roy, *IEEE Transactions on Biomedical Engineering* (1988) 35(9):653–661. In some instances, a hemoglobin count and, therefore, the hemoglobin concentration, are available and may be employed in calculating the $CO_2$ content. If a hemoglobin count or concentration is not available, another value that is based upon experiential or otherwise known data (e.g., 11.0 g/dl) may be employed in calculating the alveolar $CO_2$ content.

In calculating $V_{CO_2}$, the FRC and alveolar deadspace of the lungs of a patient may be accounted for by multiplying the FRC by the change in end tidal partial pressure, such as by the following equation:

$$V_{CO_2\ corrected} = V_{CO_2} + FRC \times \Delta Pet_{CO_2}/P_{bar},$$

where $\Delta Pet_{CO_2}$ is the breath-to-breath change in $Pet_{CO_2}$.

Baseline $Pet_{CO_2}$ and $V_{CO_2}$ values, which are also referred to as "before re-breathing $Pet_{CO_2}$" and "before re-breathing $V_{CO_2}$," respectively, occur during normal breathing and may be calculated as the average of a group of samples taken before the re-breathing process (e.g., the average of all samples between about 27 and 0 seconds before the start of a known re-breathing process). A $V_{CO_2}$ value, which is typically referred to as "during re-breathing $V_{CO_2}$," is calculated during the re-breathing process. "During re-breathing $V_{CO_2}$," may be calculated as the average $V_{CO_2}$ during the interval of 25 to 30 seconds into the re-breathing period.

The content of $CO_2$ in the alveolar blood during the re-breathing process may then be calculated by employing a regression line, which facilitates prediction of the stable, or unchanging, content of alveolar $CO_2$. Preferably, $PA_{CO_2}$ is plotted against the breath-to-breath change in content of alveolar $CO_2$ ($\Delta CA_{CO_2}$). A graph line that is defined by the plotted points is regressed, and the intersection between $PA_{CO_2}$ and zero $\Delta CA_{CO_2}$ is the predicted stable content of alveolar $CO_2$.

Pulmonary capillary blood flow may then be calculated as follows:

$$Q_{pcbf} = \frac{[\text{before re-breathing } V_{CO_2} - \text{during re-breathing } V_{CO_2}]}{[\text{during re-breathing } C_{A_{CO_2}} - \text{before re-breathing } C_{A_{CO_2}}]}.$$

Figure 11:
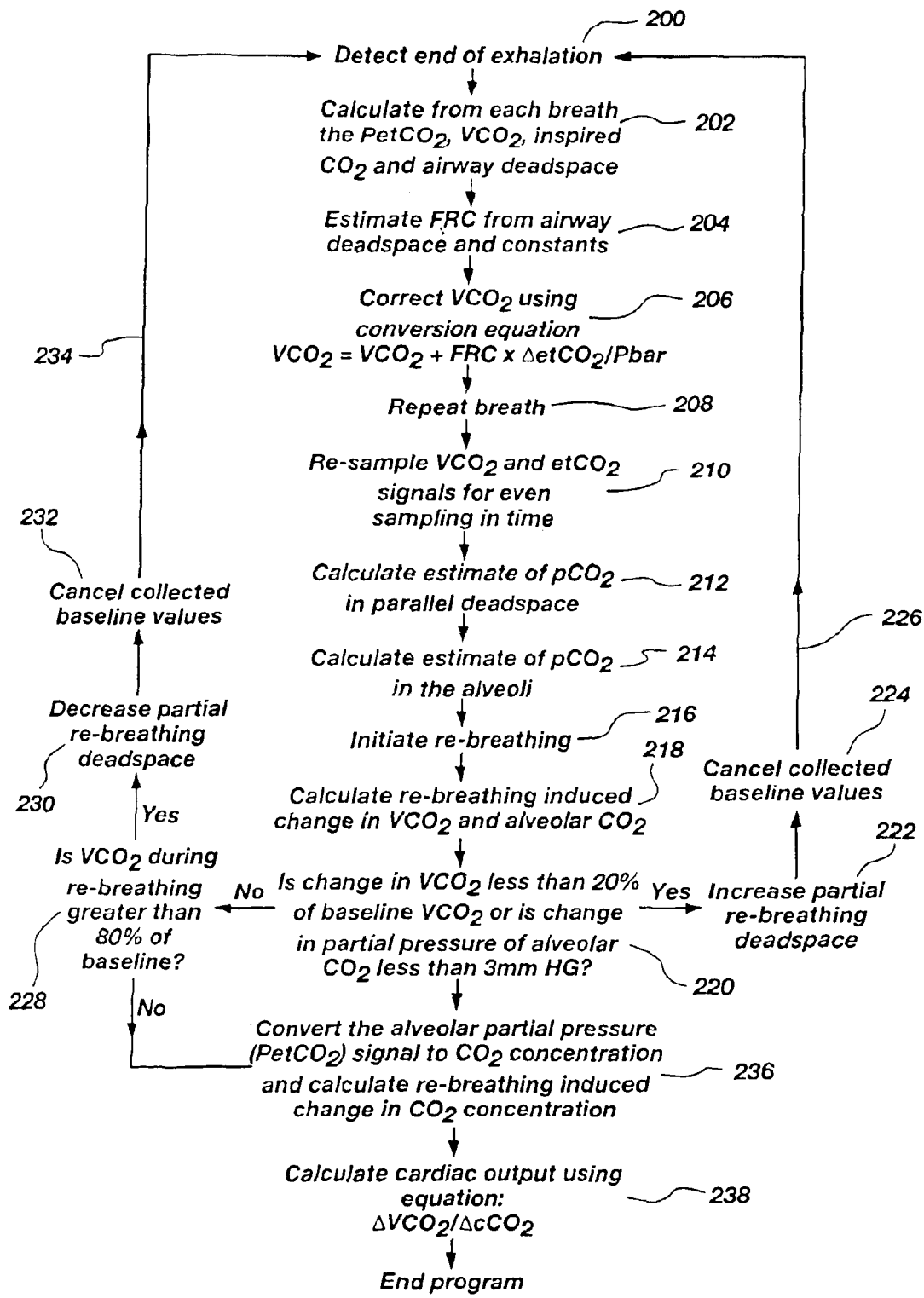
FIG. 11 is a flow diagram that illustrates the calculations made in the method of the present invention to determine cardiac output or pulmonary capillary blood flow by employing the measured values during both normal breathing and partial re-breathing.

Operation Logic of a Computer Program for Determining Cardiac Output or Pulmonary Capillary Blood Flow The operation logic of an exemplary computer program that directs the execution of the method of the present invention is briefly illustrated in the flow diagram of FIG. 11. The computer 76 (see FIG. 3) may be programmed to detect the end of an exhalation, at 200, at which point the computer 76 collects data from the carbon dioxide sensor 74 and the flow meter 72 (see FIG. 3) and calculates $Pet_{CO_2}$, $V_{CO_2}$, the fraction of inspired $CO_2$, and the airway deadspace values at 202. The computer 76 then calculates FRC, at 204, according to the previously described equation, and in accordance with the program. The program also directs the computer 76 to correct the $V_{CO_2}$ value, at 206, in accordance with the previously described equation. At determined intervals of time (e.g., two seconds), the $CO_2$ and $V_{CO_2}$ values are re-calculated, at 210, to provide data samples at evenly spaced times, not on the respiratory rate, which may be variable. This technique is typically referred to as "re-sampling" the data.

The computer 76, in accordance with the program, then calculates the estimated partial pressure of $CO_2$ ($P_{CO_2}$) in the parallel deadspace, at 212, and calculates the estimated $P_{CO_2}$ in the alveoli, at 214, using the equations described previously. At that point, re-breathing is initiated, at 216, and a deadspace volume is introduced in the re-breathing circuit. Again, the computer 76, in accordance with the programming thereof, collects data from the carbon dioxide sensor 74 and the flow meter 72 (see FIG. 3) and, from that data, determines the change in $V_{CO_2}$ and the change in partial pressure of alveolar $CO_2$ ($PA_{CO_2}$) induced by the introduction of the deadspace, at 218. If the calculated change in $V_{CO_2}$ is less than a predetermined minimum percentage (e.g., 20%) or exceeds a predetermined maximum percentage (e.g., 80%) of the baseline $V_{CO_2}$, or if the change in partial pressure of alveolar $CO_2$ is less than or exceeds predetermined threshold minimum and maximum pressures (e.g., 3 mm Hg or 20 mm Hg), determined at 220, then the operator is notified to accordingly modify the volume of the partial re-breathing deadspace, at 222. Baseline values may then be canceled, at 224 or 232, then recalculated, as suggested by arrow 226 or arrow 234. Alternatively, the computer 76 may signal mechanical or electromechanical means associated with the adjustable deadspace to automatically modify the volume thereof.

Upon proper adjustment of the adjustable deadspace and the recalculation of baseline $Pet_{CO_2}$, $V_{CO_2}$, inspired $CO_2$ and airway deadspace values, the alveolar partial pressure ($PA_{CO_2}$) is converted by the software program to $CO_2$ content of the alveolar (pulmonary) capillaries ($CA_{CO_2}$ or $Cc'_{CO_2}$). The change in the $CO_2$ content of the alveolar blood induced by having the patient re-breathe a volume of previously exhaled gases from the deadspace is then calculated, at 236. From these values, the cardiac output or pulmonary capillary blood flow of the patient may be calculated, at 238, in accordance with the previously described equation or otherwise, as known in the art.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby within their scope.

What is claimed is:

1. A method for estimating the cardiac output of an individual, comprising:
    determining a carbon dioxide elimination ($V_{CO_2}$) of the individual for a before re-breathing period and for a during re-breathing period;
    calculating a carbon dioxide elimination difference between the carbon dioxide elimination of the before re-breathing period and the carbon dioxide elimination of the during re-breathing period;
    estimating a partial pressure of carbon dioxide in alveoli ($P_ACO_2$) of the individual for the before re-breathing period and for the during re-breathing period based on partial pressure of end tidal carbon dioxide ($PetCO_2$) measurements of the individual during the before re-breathing period and during the during re-breathing period, respectively;
    converting each estimation of the partial pressure of carbon dioxide in alveoli to a carbon dioxide content ($C_{CO2}$);
    calculating a carbon dioxide content difference between the carbon dioxide content of the before re-breathing period and the carbon dioxide content of the during re-breathing period; and
    dividing the carbon dioxide elimination difference by the carbon dioxide content difference to estimate cardiac output.

2. The method of claim 1, wherein determining the carbon dioxide elimination comprises accounting for at least one of serial deadspace and parallel deadspace.

3. The method of claim 1, wherein determining the carbon dioxide elimination comprises accounting for functional residual capacity.

4. The method of claim 3, wherein accounting for functional residual capacity comprises determining a corrected carbon dioxide elimination ($V_{CO_2\ corrected}$) during at least one of the before rebreathing period and the during rebreathing period as follows:

$$V_{CO_2\ corrected} = V_{CO_2} + FRC \times \Delta Pet_{CO_2}/P_{bar},$$

where $V_{CO_2}$ is the carbon dioxide elimination that has been determined, $\Delta Pet_{CO_2}$ is the breath-to-breath change in $Pet_{CO_2}$, and $P_{bar}$ is barometric pressure.

5. The method of claim 1, wherein determining the carbon dioxide elimination for at least one of the before rebreathing period and the during rebreathing period comprises determining an average carbon dioxide elimination over a period of time.

6. The method of claim 5, wherein determining the average carbon dioxide elimination over a period of time comprises determining the average carbon dioxide elimination over a plurality of breaths.

7. The method of claim 5, wherein determining the average carbon dioxide elimination is effected at at least about twenty-five seconds into the during rebreathing period.

8. The method of claim 1, wherein estimating the partial pressure of carbon dioxide in alveoli includes accounting for at least one of functional residual capacity and carbon dioxide in parallel deadspace.

9. The method of claim 8, wherein accounting comprises employing the following formula:

$$PDS_{CO_2 PDS}(n) = [FRC/(FRC + V_t)] \cdot P_{CO_2 PDS}(n-1) + \\ (P_{bar} \cdot ([Vi_{CO_2} + \text{deadspace} \cdot (Pet_{CO_2}(n-1)/\\ P_{bar})]/V_t)[V_t/(V_t + FRC)]),$$

where (n) represents one breath, (n−1) represents a prior breath, FRC is the functional residual capacity, $V_t$ is the tidal volume, $Vi_{CO_2}$ is the volume of inspired carbon dioxide, $P_{CO_2 PDS}$ is the partial pressure of carbon dioxide in the parallel deadspace, and $P_{bar}$ is barometric pressure.

10. The method of claim 1, wherein converting at least one estimation of the partial pressure of carbon dioxide in alveoli to a carbon dioxide content comprises predicting a stable carbon dioxide content.

11. The method of claim 10, wherein predicting the stable carbon dioxide content comprises plotting the partial pressure of carbon dioxide in alveoli from at least one of the before rebreathing phase and the during rebreathing phase against a breath-to-breath change in a content of carbon dioxide in blood in the alveolar capillaries ($\Delta C_A CO_2$).

12. A method for estimating the cardiac output of a subject, comprising:
    estimating a carbon dioxide elimination of the subject for a before re-breathing period and for a during re-breathing period;
    estimating a carbon dioxide content in blood passing by the alveoli of the subject for the before re-breathing period and for the during re-breathing period;
    dividing a difference between carbon dioxide elimination from the before and during rebreathing periods by a difference between carbon dioxide content from the before and during rebreathing periods to estimate cardiac output.

13. The method of claim 12, wherein estimating the carbon dioxide elimination or estimating the carbon dioxide content for at least one of the before and during rebreathing periods comprises considering at least one of serial deadspace, parallel deadspace, and functional residual capacity.

14. A method for estimating the cardiac output of a subject, comprising:
    estimating a carbon dioxide elimination of the subject and a carbon dioxide content of blood of the subject during baseline respiration;
    providing for a change in effective ventilation of the subject;
    estimating a carbon dioxide elimination of the subject and a carbon dioxide content of blood of the subject following the change in effective ventilation;
    and dividing a change in the carbon dioxide elimination from before to after the change in effective ventilation by a change in the carbon dioxide content from before to after the change in effective ventilation to estimate cardiac ouput.

15. The method of claim 14, wherein providing for the change in effective ventilation comprises causing the subject to rebreathe previously exhaled gases.

16. The method of claim 14, wherein providing for the change in effective ventilation comprises having the subject inhale gases including an above-ambient amount of carbon dioxide.

17. The method of claim 14, wherein estimating the carbon dioxide elimination or estimating the carbon dioxide content before or after the change in effective ventilation comprises considering at least one of serial deadspace, parallel deadspace, and functional residual capacity.

* * * * *